United States Patent [19]

Young

[11] Patent Number: 4,758,577
[45] Date of Patent: Jul. 19, 1988

[54] 4-(5H-DIBENZO[A,D]CYCLOHEPTEN-5-YL)PIPERIDINE COMPOUNDS FOR TREATING CARDIOVASCULAR DISORDERS

[75] Inventor: Steven D. Young, Lansdale, Pa.

[73] Assignee: Merck & Co., Inc., Rahway, N.J.

[21] Appl. No.: 596,958

[22] Filed: Apr. 5, 1984

[51] Int. Cl.$^4$ .................. A61K 31/445; C07D 211/22; C07D 211/14

[52] U.S. Cl. .................................. 514/325; 514/249; 514/318; 544/350; 546/194; 546/203; 546/204

[58] Field of Search ....................... 546/203, 204, 194; 544/350; 424/267, 250; 514/249, 318, 325

[56] References Cited

U.S. PATENT DOCUMENTS

| | | | |
|---|---|---|---|
| 2,985,660 | 5/1961 | Judd et al. | 546/203 |
| 3,014,911 | 12/1961 | Engelhardt | 546/203 |
| 3,476,758 | 11/1969 | Fouché | 546/203 |
| 3,476,761 | 11/1969 | Fouché | 546/203 X |
| 4,356,184 | 10/1982 | Deason et al. | 546/203 X |

FOREIGN PATENT DOCUMENTS 746508 11/1966 Canada .................................. 546/203

OTHER PUBLICATIONS

Engelhardt, E. et al., *J. Med. Chem.* 8, pp. 829–835 (1965).
Merck Index, vol. 10, pp. 398–399 (1983).
Lowe, D. et al., *Br. J. Pharmac.*, 74, pp. 651–663 (1981).
Young, S. et al., *J. Org. Chem.*, 50, 399 (1985).

*Primary Examiner*—Richard A. Schwartz
*Attorney, Agent, or Firm*—Alice O. Robertson; Michael C. Sudol

[57] ABSTRACT

Novel 4-(5H-dibenzo[a,d]cyclohepten-5-yl)piperidine compounds are disclosed. The compounds have the property of inhibiting calcium induced contraction of the smooth muscle.

18 Claims, No Drawings

4-(5H-DIBENZO[A,D]CYCLOHEPTEN-5-YL)PIPERIDINE COMPOUNDS FOR TREATING CARDIOVASCULAR DISORDERS

DESCRIPTION OF THE INVENTION

The present invention is directed to novel compounds of the formula:

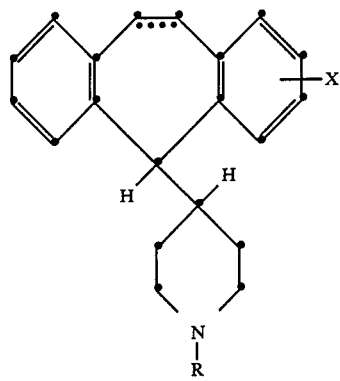
(I)

wherein
the ···· bond designation between the 10 and 11 positions indicates that the bond may be a saturated single bond or an unsaturated double bond,
X is hydrogen, halogen, trifluoromethyl or lower alkoxy,
R is selected from the group consisting of:
(a) a substituted aralkyl group represented by the formula

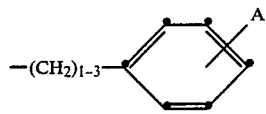

wherein A is di(lower alkyl)amino or lower alkoxy;
(b) an aralkenyl group represented by the formula:

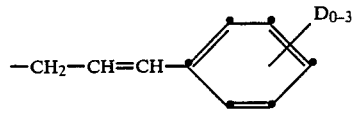

wherein D is lower alkoxy;
(c) a nitrogen containing alkyl group represented by the formula

—CH$_2$CH$_2$Y wherein Y is —CN,

or —CH$_2$NH$_2$;
(d) an acyl group represented by the formula:

wherein R' is lower alkyl, substituted lower alkyl, phenyl or substituted phenyl, styryl or substituted styryl;
(e) an imido group represented by the formula:

(f) a formyl group represented by the formula:

wherein Z is oxygen or sulfur;
(g) an alkylsulfonyl group represented by the formula:

—SO$_2$R'' wherein R'' is lower alkyl;
(h) a heteroaryl group represented by the formula

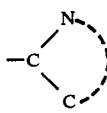

wherein the dotted lines represent a residue of a heteroaromatic ring;
and acid addition salts thereof.

The expression "lower alkyl" and "lower alkoxy" hereinbefore employed is meant to refer to radicals having 1 to 6 carbon atoms, inclusive. The expression "substituted lower alkyl" is meant those lower alkyl groups which are substituted with halogen or ω-carboxy. The expression "substituted phenyl" is meant phenyl groups which are substituted with halogen and lower alkyl. By "halogen" is meant any of the halogens, i.e. fluorine, chlorine, bromine or iodine. By "heteroaryl" is meant a ring-nitrogen bearing aromatic group which includes condensed rings and which may be substituted such as with halogen.

A preferred embodiment of the present invention is that in which the linkage between $C_{10}$ and $C_{11}$ is unsaturated so that the group is —CH═CH— and when X is not hydrogen, it is in the 3-position as represented by the following formula:

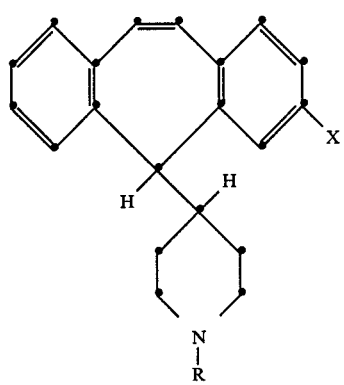
(IA)

The acid addition salts are those of non-toxic, pharmaceutically acceptable acids and include salts of inorganic acids such as hydrochloric, hydrobromic, hydroiodic, phosphoric, sulfuric, nitric and the like, and organic acids such as acetic, propionic, glycolic, pamoic, pyruvic, malonic, succinic, maleic, fumaric, malic, tartaric, citric, mandelic, benzoic, cinnamic, methanesulfonic, ethanesulfonic, salicylic, p-toluenesulfonic, cyclohexanesulfamic, and the like and include acids related to the pharmaceutically acceptable salts listed in Journal of Pharmaceutical Sciences, 66, 2 (1977) and incorporated herein by reference.

In view of the non-planar configuration of the compounds of the present invention and in view of the presence of a chiral center when X is other than hydrogen, the compounds exist in several isomeric forms.

The compounds useful in the compositions and methods of the present invention include the various isomeric forms including mixtures of isomers in various proportions and when the compound is named without designation as to a specific isomer or to a racemic mixture or to a specific mixture of isomers, it is intended to be a generic designation embracing all isomers and mixtures of isomers.

Regarding the isomeric forms, it has been found that when X is hydrogen, and R is other than hydrogen, although there is no chiral center, the compound may be obtained in two isomeric forms as a result of restricted conformational mobility. Although conformational isomers are possible when R is hydrogen, it appears that one form is too unstable to be isolated using the present synthetic method. The two isomers may be represented by the following formulas:

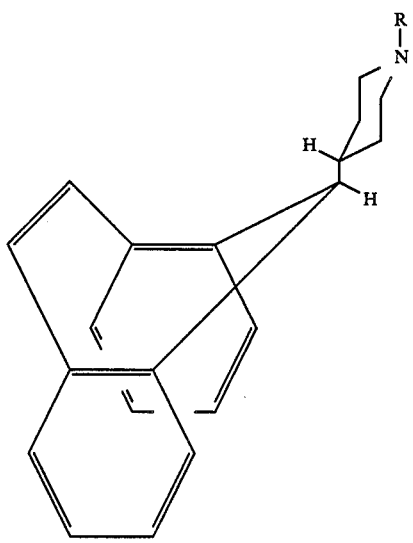
(A)

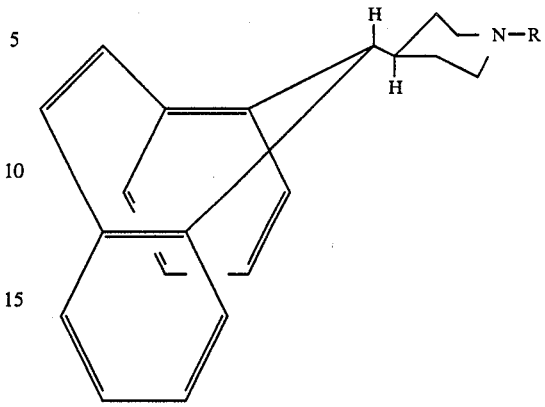
(B)

(A) may be referred to as the equatorial form, then (B) may be designated the axial form. Whether the isomer is to be characterized as equatorial or axial depends on the choice of the reference group at the 5-position. In the present application, the hydrogen (proton) attached to the 5-position is selected as the reference group. When the hydrogen is in equatorial relationship to the four carbons of the dibenzocycloheptene ring system which are common to the cycloheptene and benzene rings, the isomer has been designated as the equatorial isomer. These isomers are obtained by employing different methods of synthesis as hereinafter described. It has been found further at (B) may be converted to (A) by heating but that the reverse conversion does not occur by the application of heat.

When X is other than hydrogen, not only are there two isomeric forms as a result of restricted conformational mobility

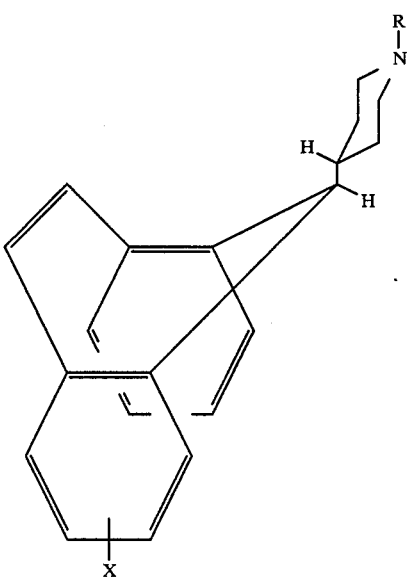
(C)

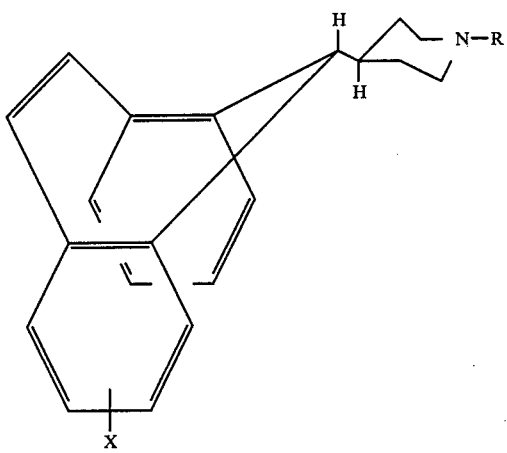

(D)

but there are also enantiomers possible for each of the isomeric forms

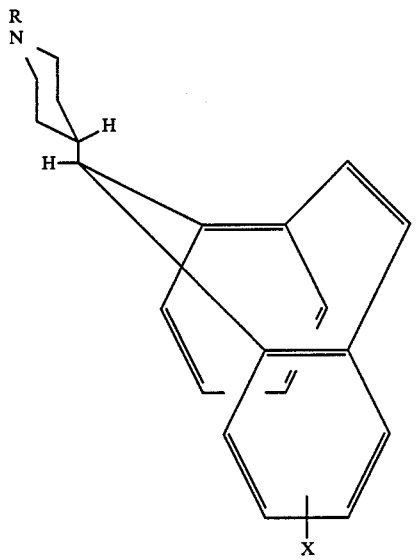

(C')

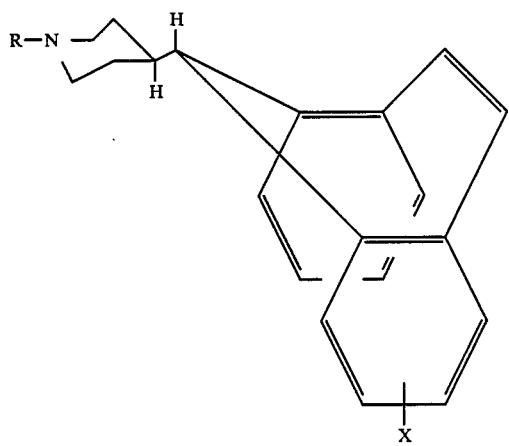

(D')

Thus, (C) and (C') are mirror images and (D) and (D') are mirror images. The absolute configuration and conformation may be determined by X-ray diffraction methods. In addition to the foregoing isomers the occurrence of which are common to all the compounds, the compounds in which R is an aralkenyl group, can be as cis or trans isomers. The preferred configuration is the trans isomer. All the possible isomers and their preparation constitutes an aspect of the present invention. Hereinafter, when reference is made generically to the conformational isomers of Formula I, $I_{eq}$ is employed to refer to the equatorial isomer and $I_{ax}$ to refer to the axial isomer.

The products of the present invention which are free bases are solids, soluble in most organic solvents and in acidic media. The products which are acid addition salts are crystalline solids.

The compounds of the present invention have useful pharmacological properties rendering them useful for therapeutic applications in pharmaceutical compositions. The compounds have shown properties which would render them useful as calcium entry blockers thereby adaptable for application in the chemotherapeutic treament of cardiovascular disorders caused by high cellular concentration of $Ca^{++}$. The compositions and methods constitute an aspect of the present invention.

The compounds of Formula I may be prepared by reacting a 4-(5H-dibenzo[a,d]cyclohepten-5-yl)piperidine compound (II) of the formula:

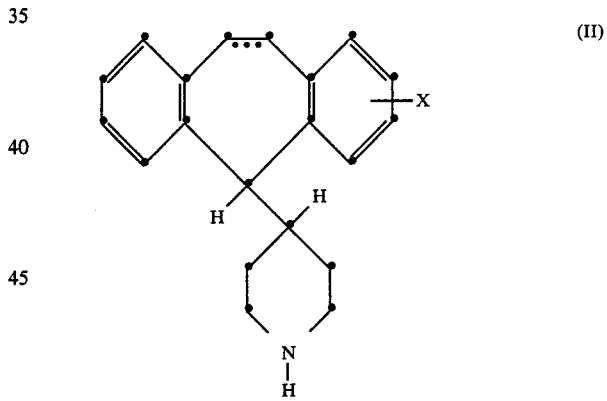

(II)

with an R group introducing compound (III) by various methods depending on the nature of the substituent to be placed on the piperidine nitrogen.

The reactant 4-(5H-dibenzo[a,d]cyclohepten-5-yl)piperidine compounds of Formula II are solids which may be prepared from the appropriate 5H-dibenzo[a,d]-cyclohepten-5-one by reducing the ketone to the corresponding alcohol i.e. the hydroxy compound, then treating the hydroxy compound with thionyl chloride to produce a 5-chloro compound which then is reacted with a Grignard reagent of 1-methyl-4-chloropiperidine to produce the N-methyl compound which is demethylated with cyanogen bromide followed by acid hydrolysis to produce the desired starting material (II) according to the scheme below and as subsequently more fully described.

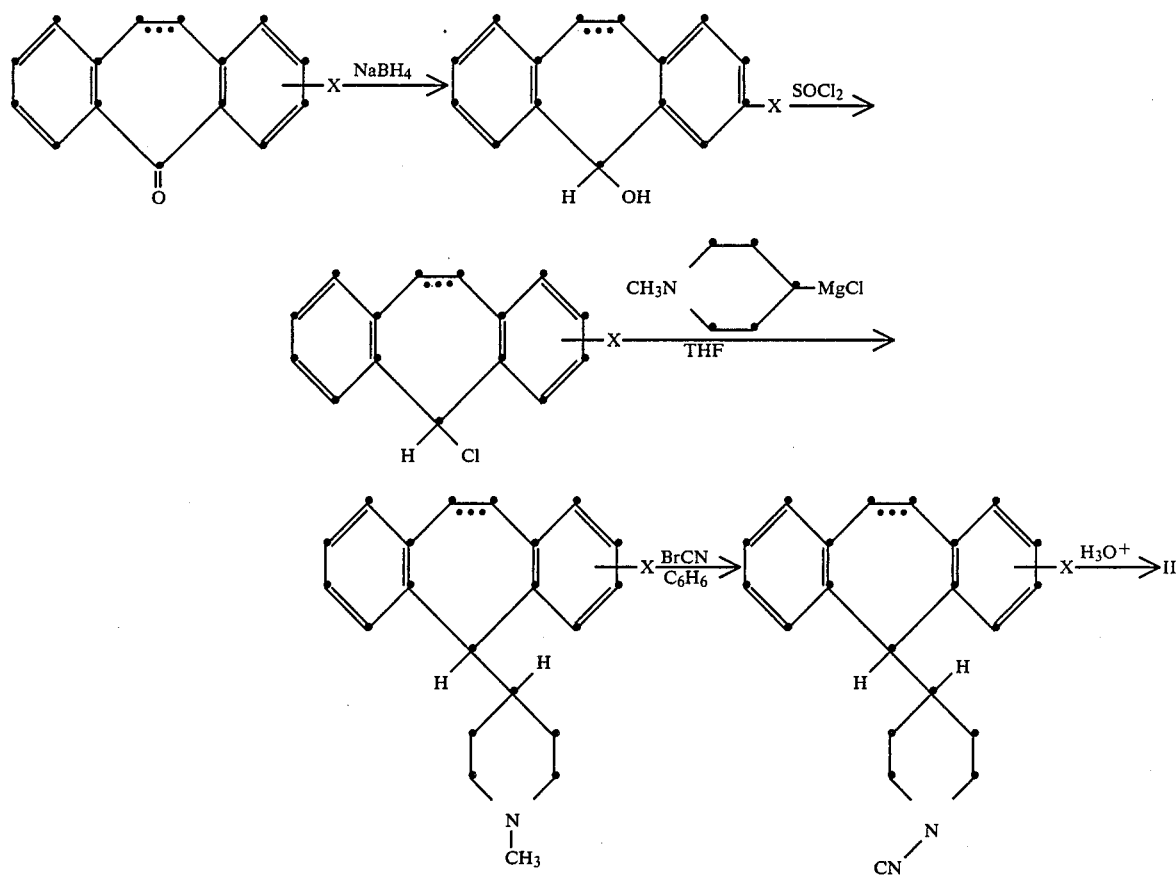

Reactant 4-(5H-dibenzo[a,d]cyclohepten-5-yl)piperidine compound of Formula II prepared in this manner is in the form of the more stable equatorial isomer and therefore are the ultimate compounds of the present invention. Preparation of the axial isomers are subsequently described.

When the compounds of Formula I are those in which R is an aralkyl group and which may be represented by Formula Ia

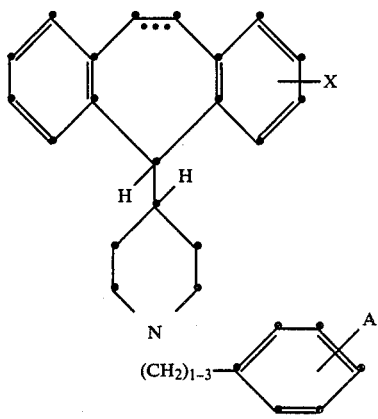

they may be prepared by reductive alkylation or conventional alkylation.

If the compounds are prepared by reductive alkylation, the piperidine compound (II) is reacted with an aldehyde reactant (IIIa)

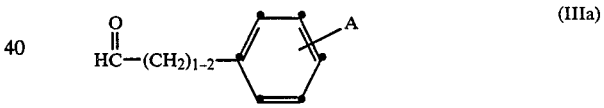

in the presence of a reductant. The reaction may be carried out by intimately mixing piperidine compound (II), aldehyde reactant (IIIa), reductant and solvent. Suitable reductants include sodium cyanoborohydride, aluminum/mercuric chloride, and the like. Suitable solvents include methanol, ethanol, isopropanol and the like. The exact proportions of II and IIIa is not critical. Good results have been obtained employing substantially equimolar amounts of piperidine compound and aldehyde reactant. The reductant is employed in excess, from three to ten-fold molar excess. If the reductant is sodium cyanoborohydride, the amount is closer to threefold; if aluminum/mercuric chloride it is about ten-fold molar excess of aluminum with 0.05 percent mercuric chloride. Generally, stirring is carried out at ambient temperatures for from several hours to overnight. After completion of the reaction, the product is recovered from the reaction mixture by conventional procedures. If aluminum/mercuric chloride or other insoluble reductant is employed, the unreacted excess and salts are first filtered off, the reaction mixture of filtrate then is diluted with a water-immiscible solvent, washed with water and appropriate aqueous solutions such as aqueous bisulfite, aqueous base and brine, then dried, the organic solvent vaporized and the product recovered as residue. Further purification may be employed such as washing with solvent, recrystallization, treatment with adsorbent such as silica gel or charcoal, column-chromatography, Still or flash chromatography (J. Org. Chem. 43, 2923 (1978)) and the like.

Alternatively, the compounds represented by Formula Ia may be prepared by conventional alkylation procedure wherein the piperidine compound (II) is reacted with an alkyl halide (IIIa')

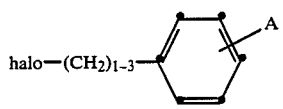
(IIIa')

in the presence of a base in a solvent medium. The hydrogen halide acceptor base may be a tertiary amine such as triethylamine, diisopropyl ethylamine, trimethylamine, pyridine, collidine and the like or may be an inorganic base. Suitable solvents include polar solvents such as ethanol, isopropanol, n-butanol and the like, or aqueous mixtures if an inorganic base is employed. Generally an excess of the alkyl halide is employed, and the reactants and the base are mixed together in the solvent and refluxed for time sufficient to complete the reaction with the formation of the desired cycloheptenylpiperidine compounds of Formula Ia.

Compounds of the present invention in which R is an aralkenyl group and which may be represented by Formula Ib

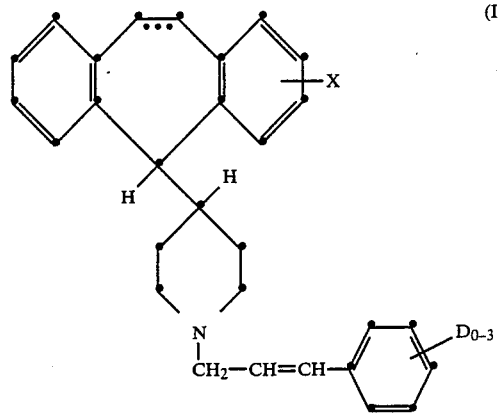
(Ib)

may be prepared by employing an acylated piperidine compound Id in which R' is styryl or substituted styryl as subsequently described or by first reacting the piperidine compound II with an aralkenoyl halide (IIIbi) to produce an acylated piperidine compound (Ibi) which is then subjected to the action of a reducing agent as seen in the following reaction sequence:

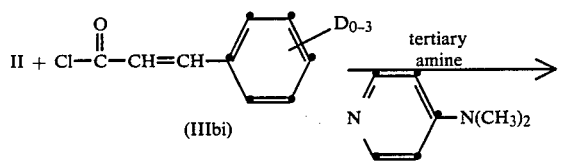
(IIIbi)

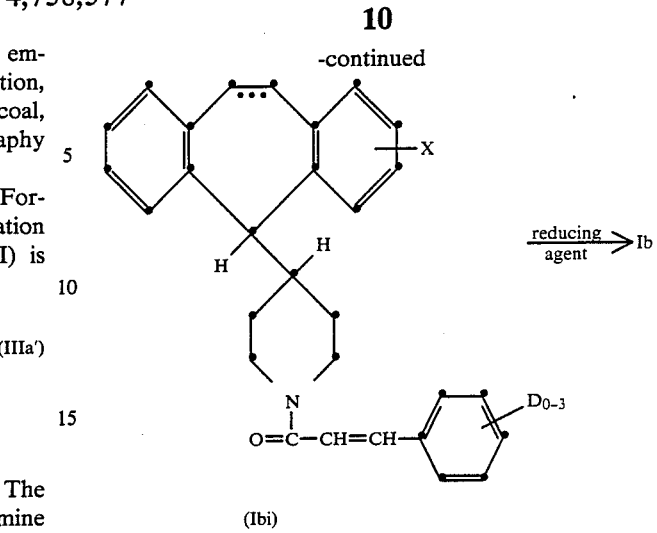
(Ibi)

The reaction may be carried out by adding the aralkenoyl halide to a stirred mixture of piperidine compound II, a tertiary-organic base and 4-dimethylaminopyridine catalyst, and continuing the mixing for from about 0.5 to several hours at room temperature to obtain an aralkenoyl piperidine compound in the reaction mixture. For the reaction, the piperidine compound II and aralkenoyl halide are employed in substantially equimolar proportions. The reaction is carried out in the presence of two- to fourfold molar excess of a tertiary amine to bind the hydrogen halide by-product which is formed. Suitable amines include triethylamine, trimethylamine, diisopropylethylamine, tripropylamine, pyridine, collidine and the like. There is also added to the reaction mixture 4-dimethylaminopyridine as catalyst. A solvent is employed in the reaction. Suitable solvents include methylene chloride, chloroform, carbon tetrachloride and the like. The aralkenoyl piperidine intermediate (Ibi) may be recovered from the reaction mixture by diluting the mixture with an inert solvent such as ether, washing the ethereal solution with appropriate aqueous reagents such as dilute hydrochloric acid, bicarbonate and brine, drying, and then vaporizing the solvent.

The intermediate aralkenoyl piperidine compound (Ibi) then is reacted with a reducing agent to obtain the desired product Ib. Lithium aluminum hydride is a convenient and suitable reagent although other reducing agents may be employed. When employing lithium aluminum hydride, the reaction is carried out in a solvent in an inert atmosphere. Suitable solvents are ethereal solvents, preferably tetrahydrofuran but also diethyl ether, diisopropyl ether, and the like. Argon or nitrogen atmosphere is provided. Generally from about 1.5 to 2.5 molar excess of the lithium aluminum hydride is employed. Lithium aluminum hydride in solid form may be added in small portions to a solution of the aralkenoylpiperidine intermediate in ethereal solution. Alternatively, a solution of the aralkenoylpiperidine may be contacted with a solution of the reducing agent. The addition is carried out at ambient temperature. After completion of the addition, the resulting mixture is stirred for time sufficient to complete the reaction. The entire operation may be carried out at ambient temperature or may be heated to the reflux temperature of the solution to complete the reaction. Usually the stirring is carried out for from several hours to conveniently overnight. After completion of the reaction, The mixture may be diluted with solvent and the reaction quenched employing the "n, n, 3n" method, and the product recovering employing conventional procedures. The product may be purified by conventional methods as previously described.

The "n, n, 3n" method for quenching the reaction is described on page 584 of Fieser and Fieser, "Reagent for Organic Synthesis" John Wiley and Sons, Inc., New York, 1967. Briefly, it entails treating the stirred reduction mixture from n grams of lithium aluminum hydride by successive dropwise addition of n milliliters of water n milliliters of 15 percent sodium hydroxide and 3n milliliters of water producing a granular precipitate which can be readily filtered and washed.

The compounds of the present invention in which R is Y—CH$_2$—CH$_2$— and which may be represented by the formula:

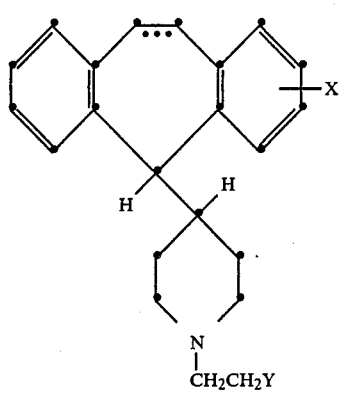
(Ic)

are preferably prepared by specific methods wherein one may be an intermediate in the preparation of the other.

Those compounds in which Y is CN and represented by the formula

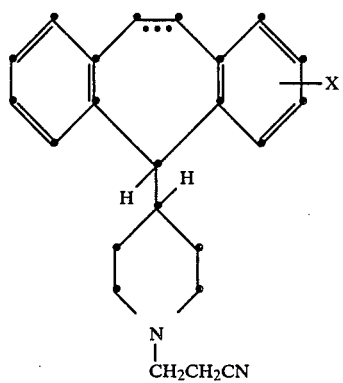
(Ic')

may be prepared by reacting the piperidine compound II with acrylonitrile. The reaction is conveniently carried out by intimately mixing piperidine compound II, acrylonitrile and solvent for time sufficient to complete the reaction with the formation of the nitrile compound (Ic'). Suitable solvents for the reaction include benzene, toluene, xylenes, and the like. The acrylonitrile reactant is employed in excess, suitably about a two-fold molar excess. The reaction is preferably carried out at elevated temperatures, conveniently at the reflux temperature of the solution. The reaction is usually substantially complete in several hours, the actual time can be determined readily by thin layer chromatographic (TLC) analysis of the reaction mixture to determine extent of consumption of the starting material. After completion of the reaction, the product is recovered as residue by vaporizing the solvent and unreacted acrylonitrile. The residue then may be purified by conventional procedures.

Those compounds in which Y is

and represented by the formula

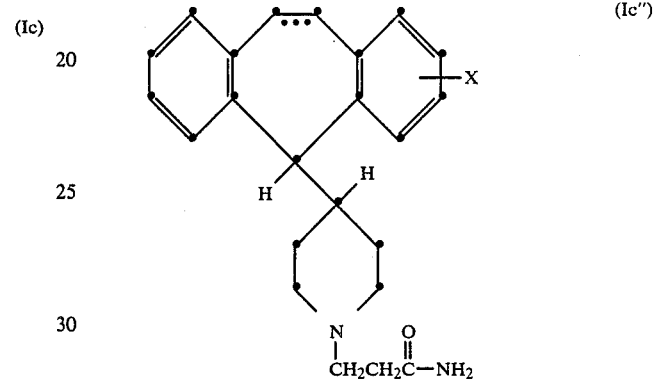
(Ic")

may be prepared by a controlled hydrolysis of the nitrile (Ic') but is best prepared by an addition reaction between the piperidine compound II and acrylamide (IIIc"). The reaction is conveniently carried out by intimately mixing piperidine compound II, acrylamide and tertiary amine catalyst in a solvent for time sufficient to complete the reaction with the formation of the amide compound (Ic").

The conditions for carrying out the reaction are similar to that employed in the addition of acrylonitrile. Thus, molar excess of the acrylamide is employed and the reaction is carried out in an inert environment protected from atmospheric moisture at moderately elevated temperatures, preferably reflux temperature of the solution. Suitable solvents for the reaction include isopropanol, n-propanol, ethanol and the like. Suitable catalysts are tertiary amines such as triethylamine, dimethylethylamine, trimethylamine, pyridine, collidine, 4-dimethylaminopyridine, and the like.

The reaction is usually substantially complete in several hours, the actual time being readily determinable by TLC analysis of the reaction mixture. After completion of the reaction, the unreacted acrylamide and solvent are vaporized, the amide compound (Ic") recovered as residue and thereafter purified by conventional procedures.

Those compounds in which Y is —(CH$_2$)$_3$NH$_2$ and represented by the formula (Ic''')

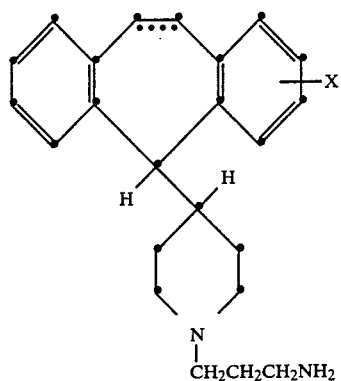
(Ic''')

may be prepared by reduction of an amide (Ic'') in which Y is

C—NH$_2$.

The reduction may be carried out by contacting the amide and the reducing agent in solution in an inert atmosphere at ambient temperature and the resulting mixture stirred for time sufficient to complete the reduction. Various reducing agents may be employed. Lithium aluminum hydride is a preferred agent. When it is the reducing agent employed, the conditions for carrying out the reaction are similar to that previously described for reduction of an amide during the preparation of compounds in which R is an aralkenyl group. Thus, with lithium aluminum hydride, the reaction may be carried out by adding the lithium aluminum hydride portionwise as solid or in solution, in an inert atmosphere to the amide compound in an ethereal solvent and intimately contacting the components at ambient or reflux temperature of the solution for time sufficient to complete the reaction. The product then may be recovered in a conventional manner after quenching the reaction as previously described.

The compounds of the present invention in which R is an acyl group and which may be represented by Formula Id

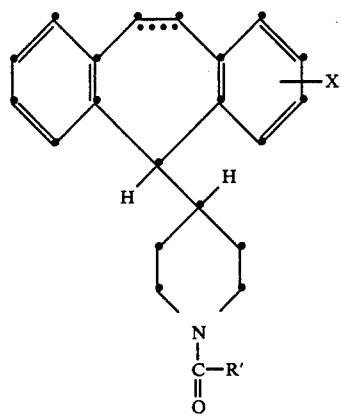
(Id)

may be prepared by the reaction of the piperidine compound II with an acyl chloride or anhydride (IIId) in the presence of a catalyst and an acid binding agent to bind the by-product hydrogen halide or other acid formed in the reaction. From equimolar to about two-fold molar excess of acid chloride is employed. Suitable catalysts include 4-dimethylaminopyridine and the like. Suitable acid binding agents are preferably tertiary amines such as those described previously in connection with alkylation. At least a two-fold molar excess of the tertiary amine is employed; a four- to fivefold molar excess may be employed. The reaction is carried out in a solution under anhydrous conditions. Suitable solvents for reaction medium include methylene chloride, carbon tetrachloride and the like.

In carrying out the reaction, the components are mixed in an inert atmosphere protected from atmospheric moisture. Depending on the activity of the acid chloride or anhydride, it may be desirable to add the acid chloride portionwise to the reaction mixture. The reaction is usually rapid and is complete in from about one-half hour to several hours. The time for completion of the reaction may be determined by TLC analysis of the reaction mixture.

After completion of the reaction, the mixture is admixed with ice and stirred with warming to ambient temperature to decompose unreacted starting acid halide or anhydride. The organic solution is separated from the aqueous solution, washed successively with aqueous hydrochloric acid, bicarbonate, and brine, then dried and the N-acyl piperidine product (Id) then is recovered by conventional procedures. Thereafter, the product may be purified using any one or a combination of conventional procedures.

The compounds of the present invention in which R is a

NH
‖
—CNH$_2$ group and which is represented by the formula

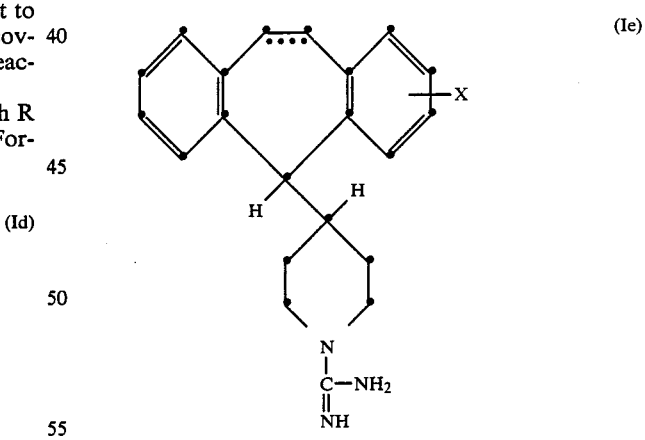
(Ie)

may be prepared by intimately mixing the piperidine reactant (II) preferably as the hydrohalide salt with cyanamide.

The hydrohalide salt of the piperidine compound II may be prepared as first step employing conventional procedures. In the reaction of the salt with cyanamide, the cyanamide is employed in excess, from about 1.5 to 2.5 molar excess. The reaction is carried out in the presence of a solvent at temperatures above about 90° C. for from 8 to 12 days. Suitable solvents include alcohol solvents such as n-butanol, n-propanol, isopropanol and the like.

In carrying out the reaction, the piperidine compound II hydrohalide, cyanamide and solvent are heated together at reflux temperature for time sufficient to complete the reaction with the formation of Compound Ie in the reaction mixture usually as a solid. The solid may be recovered by conventional procedures and crystallized or recrystallized from suitable solvents, generally lower alkanols.

The compounds of the present invention which may be represented by the formula

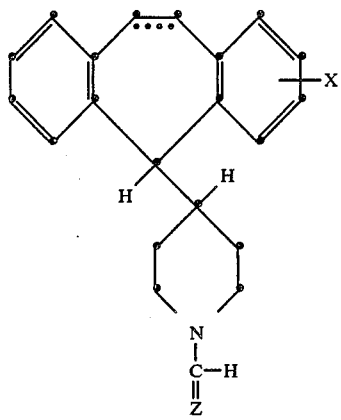

(If)

may be prepared by reacting a piperidine compound II with a dimethylformamide compound (IIIf). When Z is oxygen (If), the reactant dimethylformamide compound would be dimethylformamide itself (IIIf'). When Z is sulfur (If''), the reactant is dimethylthioformamide (IIIf'). An excess of the dimethylformamide compound is employed. When the reactant is dimethyl thioformamide, generally from about 1.5 to 2.5 molar excess is employed in a solvent as reaction medium. Suitable solvents include toluene, the xylenes, benzene and the like. When dimethylformamide is the reactant, a large excess of dimethylformamide is employed with the dimethylformamide itself serving as a solvent.

In carrying out the reaction, the components are stirred together conveniently at the reflux temperature of the solution for time sufficient to complete the reaction with the formation of the Compound If. The actual time for substantial completion of the formation of the Compound If may be determined by TLC analysis. At the temperatures employed, for the thioacyl compound, it has been found that the reaction may require several days. After completion of the reaction, the product may be recovered as residue by diluting with solvent, washing with water, drying and vaporizing the solvent. The product residue may be purified by conventional procedures.

It has been found that at the reflux temperature of dimethylformamide, the N-formyl compound may be produced even when N-arylation is intended. Thus, in attempted preparation of N-phenyl compounds from iodobenzene and copper in dimethylformamide as solvent, the N-formyl compound was produced.

Compounds of the present invention which may be represented by formula (Ig)

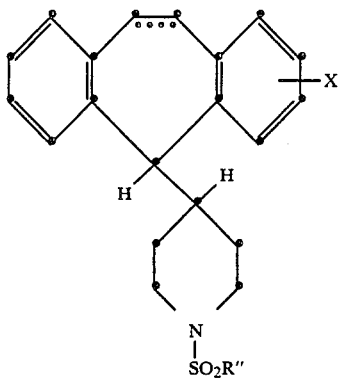

(Ig)

may be prepared by the reaction of piperidine compound II with a sulfonyl halide R"SO₂Cl (IIIg) in solvent medium in the presence of a tertiary amine to bind the acid halide by-product. The sulfonyl halide is employed in excess; generally, from about 1.5 to 2 molar excess is suitable. Suitable tertiary amines include those previously enumerated as acid binding agents. Suitable solvents are methylene chloride, carbon tetrachloride, chloroform, and the like. The reaction is preferably carried out by adding neat sulfonyl chloride dropwise to a solution containing the piperidine compound II and the tertiary amine acid binding agent. The reaction is exothermic and substantially instantaneous. After completion of the addition, the reaction mixture may be stirred for from one-half to several hours to assure completion of the reaction. At the end of this time, the product may be recovered and purified employing conventional techniques.

Compounds of the present invention which may be represented by the formula (Ih)

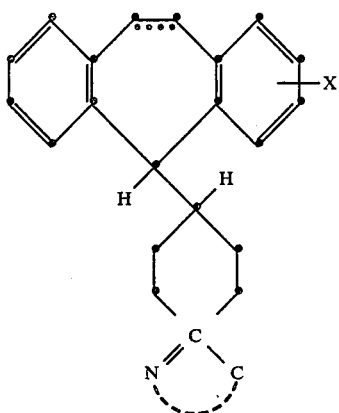

(Ih)

wherein the dotted line represents a residue of a heteroaromatic ring which may be mononuclear or polynuclear and which may contain other heterocyclic atoms and/or other substituents may be prepared by the reaction of the piperidine compound (II) and a halo-heteroaromatic compound (IIIh) in the presence of an acid binding agent and a catalyst. The acid binding agents are tertiary amines previously described. The catalyst preferably is 4-dimethylaminopyridine. The reaction is carried out in a solvent such as butanol, propanol, ethanol and the like. Approximately equimolar amounts of the reactants are employed. The reaction is conveniently carried out at reflux temperature for time sufficient for completion of the reaction. Thereafter the product may be recovered employing conventional procedures, and purified, if desired, also employing conventional procedures.

The axial isomers are not obtained by the foregoing procedures. In fact, none of the compounds are obtained as axial isomers by any currently known methods. The compounds of Formula Ia and Ib may be obtained as axial isomers by employing an appropriately substituted Grignard reagent in the following sequence of reactions:

tially in a cooled ethereal solution and thereafter at ambient temperature to obtain the magnesium halide salt of a 5H-dibenzo-[a,d]cyclohepten-5-ol which is hydrolyzed under acid conditions to obtain the hydroxy compound. The hydroxy compound may be recovered by conventional procedures. The reductive cleavage of the hydroxy group of the compounds of Formula V may be carried out by mixing the hydroxy compound with a molar excess of triethylsilane in a water-immiscible organic solvent, cooling the mixture to −40° to 0° C. and bubbling in boron trifluoride for time sufficient

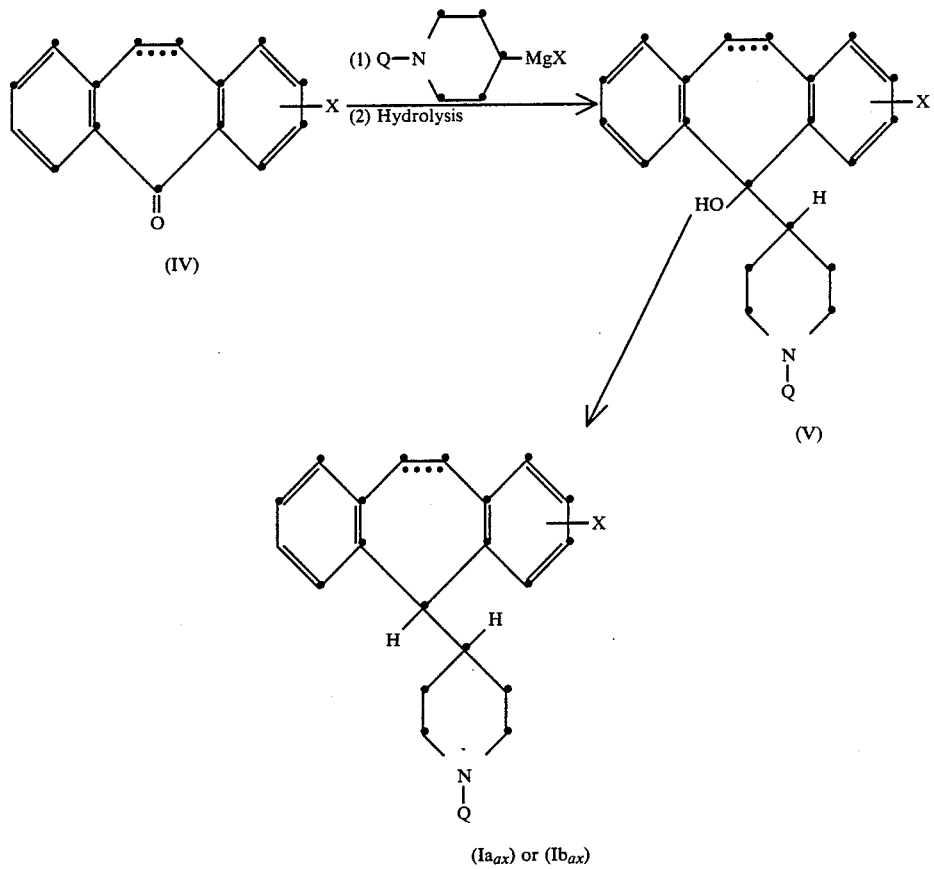

In the foregoing formulas Q represents;

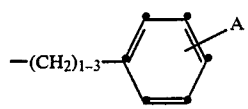

or

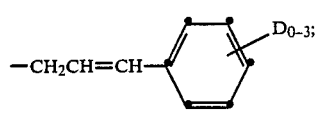

thus the formula represents compounds of Formula Ia and Ib in the axial form.

When the axial isomer is to be prepared, the preparation of the hydroxy compound from the ketone is a conventional Grignard synthesis. Thus, an appropriate 5H-dibenzo[a,d]cyclohepten-5-one (IV) is caused to react with the Grignard reagent of 1-aralkyl-4-chloropiperidine or 1-aralkenyl-4-chloropiperidine inito saturate the reaction mixture, thereafter bringing the reaction mixture gradually to ambient temperature to complete the reduction. The reaction may be quenched by adding first solid potassium carbonate, then water, and thereafter recovering the product from the organic solution employing conventional procedures.

All of the compounds of Formula I may be obtained as acid addition salts. Some of the products of the present invention are preferably isolated as acid addition salts. In other cases, they may be isolated as bases and converted into salts as desired. When salts are desired, the base product may be dissolved in a solvent such as alkanol and the appropriate acid added thereto. Usually the crystalline salt will start to form immediately and precipitate in the reaction mixture. The reaction mixture may be cooled to facilitate and/or complete the reaction.

The compounds of the present invention possess pharmacological properties adaptable for therapeutic uses. One of the properties demonstrated by the compounds is inhibition of calcium induced contraction of tracheal smooth muscle or vascular tissue. The property may be observed in a test in which segments of vascular smooth muscle obtained from male Sprague-Dawley rats are suspended in physiological salt solution in a tissue bath instrumented for recording contractions. After the tissue has been equilibrated, washed in calcium-free physiological salt solution and depolarized, 0.1 mM calcium chloride is re-added to induce contraction. After the contraction has reached a plateau, tissues are washed and a test compound or vehicle is added to determine the effect on a second contraction achieved by the above cyclic protocol. From measuring the initial contraction as well as the second contraction in the presence of the first compound, the extent of inhibition may be calculated.

The most effective compounds for inhibiting calcium induced contraction of tracheal smooth muscle or vascular tissue were rated to be those in which the carbon of the R group attached to the piperidine nitrogen at the point of attachment is in the reduced form, e.g. a methylene group, so that the group may be represented as $-CH_2G$ wherein G represents the remainder of the substituent. The most active compounds were those in which the carbon of G attached to the reduced carbon was part of an unsaturated grouping. Thus, the most active compounds, included these in which R was cinnamyl, 3,4,5-trimethoxycinnamyl and 4-dimethylaminobenzyl. The compounds having the foregoing groups demonstrated high level of activity at low level of concentrations of $10^{-7}M$ in the above described test. Thus, in the test, 4-(5H-dibenzo[a,d]cyclohepten-5-yl)-1-(4-dimethylaminobenzyl)piperidine showed 69 percent inhibition, 4-(5H-dibenzo[a,d]cyclohepten-5-yl)-1-cinnamyl-piperidine showed 70 percent and 4-(5H-dibenzo[a,d]cyclohepten-5-yl)-1-(3,4,5-trimethoxycinnamyl)piperdine showed 68 percent inhibition at $10^{-7}M$.

The compounds which were intermediate in activity were those in which the atom attached to the piperidine nitrogen was part of an acyl group. The groups were those which may be represented as

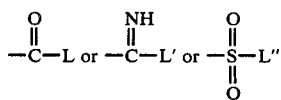

wherein L,L' and L" represents the remainder of the substituent. Compounds having these groups showed moderate to low activity at $10^{-7}M$ indicating the desirability of employing higher concentrations of these compounds. Certain of the compounds are additionally useful as intermediates in the preparation of the highly active aralkenyl compounds.

The compounds least active were the heteroaryl substituted compounds indicating higher concentration requirement.

For use in the treatment of cardiovascular diseases caused by high cellular concentration of $Ca^{++}$, a therapeutically effect amount of the 4-(5H-dibenzo[a,d]cyclohepten-5-yl)piperdine compound of Formula I or a pharmaceutically acceptable acid addition salt thereof, or compositions containing said compounds are administered to subjects with such diasease. The administration may be made orally, parenterally, by inhalation, or by suppository, and in any suitable dosage form. For oral administration, the compounds may be offered in the form of tablets or capsules with suitable dispersants and carrier materials or dispersed in a liquid carrier for administration as solution or aqueous dispersion or emulsion; for parenteral administration, the compounds may be dispersed in an appropriate liquid carrier with or without dispersing agents depending on whether a solution, emulsion or other dispersion is intended; for aerosol administration the compound may be dispersed formulated with a suitable dispersant and propellant; and for use as suppository the compounds may be dispersed in a suitable carrier. Suitable carriers and dispersants are hereinafter described.

The ratio of the compound of the present invention to carrier varies with the particular compound, purpose and the mode of administration and whether or not it is intended to be employed without dilution or modification. The dosage level of the compounds may be varied from about 0.3 mg to about 40.0 mg per kilogram of body weight per day. Daily doses in the range of 1 to 12 mg/kg are preferred.

The compounds may be administered in pharmaceutically acceptable acid addition salt form. Such acid addition salt forms exhibit the same order of activity as the free base forms and may be prepared from the free base as previously described or other conventional procedures.

The free base or salt may be formulated with a pharmaceutical carrier or diluent.

To prepare the pharmaceutical compositions of this invention, compound of Formula (I) or acid addition salt thereof, as the active ingredient, is intimately admixed with a pharmaceutically acceptable carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients may be included for purposes such as, for example, for aiding solubility or for preservation. Injectable suspensions also may be prepared, in which case appropriate liquid carriers, suspending agents and the like may be employed. The pharmaceutical compositions herein will contain, per dosage unit, e.g., tablet, capsule, powder, injection, teaspoonful and the like, from about 0.075 to about 10.0 mg of the active ingredient, and, preferably, from about 0.3 to about 4.0 mg.

The following examples illustrate the invention but are not to be construed as limiting.

EXAMPLE I 4-(5H-Dibenzo[a,d]cyclohepten-5-yl)-1-(4-dimethylaminobenzyl)piperidine

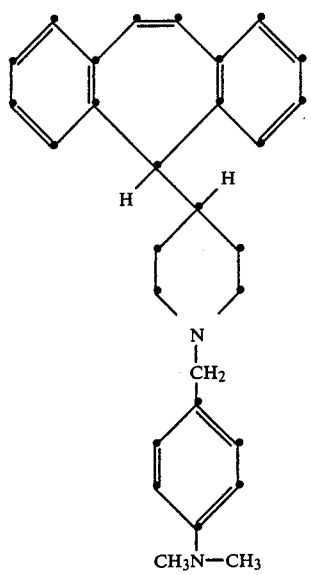

1.00 gram (3.47 millimoles) of 4-(5H-dibenzo[a,d]cyclohepten-5-yl)piperidine, 0.52 gram (3.47 millimoles) of p-dimethylaminobenzaldehyde, 0.63 gram (10.0 millimoles) of sodium cyanoborohydride and 10 milliliters of ethanol were stirred together at room temperature for 24 hours. At the end of this period, the mixture was diluted with 150 milliliters of ethyl acetate and the ethyl acetate solution washed successively with two 50 milliliter portions of 15 percent aqueous sodium bisulfite, one 50 milliliter portion of saturated sodium bicarbonate, and one 100 milliliter portion of brine and then dried over magnesium sulfate. The solvent was vaporized from the dried solution in vacuo to obtain a yellow oil. The oil was flash chromatographed on silica gel with 50/50 ethyl acetate/hexane as eluant to obtain 250 milligrams of a colorless oil which crystallized on standing overnight. The product after recrystallization from acetonitrile had a melting point of 163°–165° C. Elemental analyses of the product were as follows:

Calcd for $C_{29}H_{32}N_2$: C, 85.25; H, 7.89; N, 6.86 Found: C, 84.89; H, 7.83; N, 7.11.

EXAMPLE II 4-(5H-Dibenzo[a,d]cyclohepten-5-yl)-1-cinnamoylpiperidine and
4-(5H-Dibenzo[a,d]cyclohepten-5-yl)-1-cinnamylpiperidine and hydrogen oxalate salt

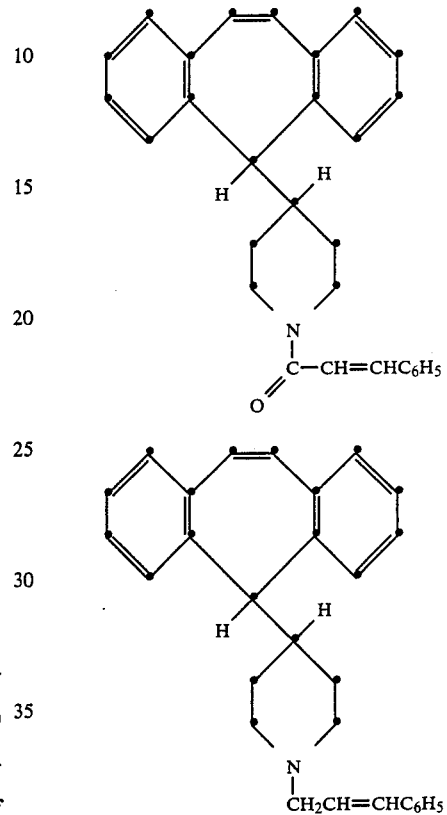

1.42 grams (5.15 millimoles) of 4-(5H-dibenzo[a,d]cyclohepten-5-yl)piperidine, 1.56 grams (15.45 millimoles0 of triethylamine, 0.06 gram (0.51 millimoles) of 4-dimethylaminopyridine and 25 milliliters of methylene chloride were stirred together for 5 minutes and to the stirred solution, 0.86 gram (5.15 millimole) of cinnamoyl chloride was added in one portion. The resulting mixture was stirred for 0.5 hour at room temperature, then diluted with 200 milliliters of ether and the ethereal solution washed successively with two 200 milliliter portions of 2N hydrochloric acid, one 200 milliliter portion of sodium bicarbonate solution and one 300 milliliter portion of brine. The washed solution was dried over magnesium sulfate, and the solvent vaporized in vacuo from the dried solution to obtain as residue 1.6 grams of 4-(5H-dibenzo[a,d]cyclohepten-5-yl)-1-cinnamoylpiperidine.

0.78 gram (20.6 millimoles) of lithium aluminum hydride was added in small portions under argon atmosphere to a solution of the above prepared cinnamoylpiperidine in 50 milliliters of dry tetrahydrofuran to obtain 4-(5H-dibenzo[a,d]cyclohepten-5-yl)-1-cinnamylpiperidine in the reaction mixture. The latter was recovered in the usual manner, i.e., diluting with tetrahydrofuran, quenching by the "n,n,3n" method, drying the solution over magnesium sulfate, vaporizing the solvent in vacuo from the filtered dried solution thereby obtaining a residue, flash chromatographing the residue on silica gel employing 75/25 ethyl acetate-hexane as eluant to produce 681 grams of a purified 4-(5H-dibenzo[a,d]cyclohepten-5-yl)-1-cinnamylpiperidine base product. The base was dissolved in methanol and a solution of 219 milligrams (1 equivalent) oxalic acid dihydrate in 2 milliliters of methanol added to the solution of the base and the resulting mixture allowed to stand overnight to obtain 4-(5H-dibenzo[a,d]cyclohepten-5-yl)-1-cinnamylpiperidine hydrogen oxalate product as crystals melting 218°-220° C. The product had elemental analyses as follows:

Calcd for $C_{29}H_{29}N\cdot C_2H_2O_4$: C, 77.31; H, 6.49; N, 2.91 Found: C, 77.32; H, 6.75; N, 3.09.

EXAMPLE III 4-(5H-Dibenzo[a,d]cyclohepten-5-yl)-1-(3-(3,4,5-trimethoxyphenyl)prop-2-en-1-yl)piperidine 0.86 gram (3.62 millimoles) of 3,4,5-trimethoxycinnamic acid and 16.3 grams (137 millimoles) of thionyl chloride were heated together at reflux temperature for 45 minutes to obtain 3,4,5-trimethoxycinnamoyl chloride. The reaction mixture was subjected to reduced pressure to vaporize excess thionyl chloride and to recover the acid chloride as residue. The acid chloride was purified by repeated dissolution in benzene and vaporizing the volatile matter. The purified acid chloride residue was dissolved in 15 milliliters of dry methylene chloride and the solution cooled to 0° C. To the solution was added a solution of 4-(5H-dibenzo[a,d]cyclohepten-5-yl)piperidine and triethylamine in 15 milliliters of methylene chloride. The resulting mixture was allowed to warm to room temperature and then stirred overnight. As the end of this time, the mixture was diluted with methylene chloride and washed successively with 2N hydrochloric acid, aqueous sodium bicarbonate and brine and thereafter dried. The dried solution was subject to reduced pressure to remove the solvent and to obtain 1.84 grams of 4-(5H-dibenzo-[a,d]cyclohepten-5-yl) 1-(3,4,5-trimethoxyphenyl)prop-2-enoyl)piperidine as a light brown foamy solid. The latter was flash chromatographed on 80 grams of silica gel employing 40/60 ethyl acetate/hexane as eluant to obtain 1.06 grams of the product as an oil.

150 milligrams (4.0 millimoles) of lithium aluminium hydride was added to 1.00 gram (2.02 millimoles) of 4-(5H-dibenzo[a,d]cyclohepten-5-yl)-1-(3,4,5-trimethoxyphenyl)prop-2-enoyl)piperidine in 20 milliliters of dry tetrahydrofuran and the mixture stirred at room temperature under argon atmosphere for 17 hours to obtain a 4-(5H-dibenzo[a,d]cyclohepten-5-yl)-1-(3-(3,4,5-trimethoxyphenyl)prop-2-en-1-yl)piperidine in the reaction mixture. The reaction was quenched employing the "n,n,3n" method and thereafter worked up in the usual manner to obtain 0.79 gram of crude product. This was chromatographed on silica gel employing 80/20 ethyl acetate/hexane as eluant to obtain 351 grams of purified product which after crystallization from ethyl acetate-hexane was found to have a melting point of 146°-148° C. 360 MH$_2$ NMR determination showed the product to have ⅓ mole water of crystallization. Elemental analyses were as follows:

Calcd. for $C_{32}H_{35}NO_3\cdot\frac{1}{3}H_2O$: C, 78.82; H, 7.37; N, 2.87. Found: C, 78.99; H, 7.77; N, 3.04.

EXAMPLE IV 4-(5H-Dibenzo[a,d]cyclohepten-5-yl)-1-(2-cyanoethyl)piperidine

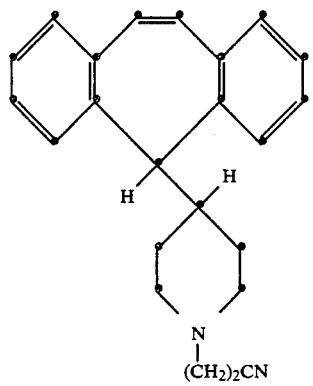

A solution of 1.00 gram (3.62 millimoles) of 4-(5H-dibenzo[a,d]cyclohepten-5-yl)piperidine in 20 milliliters of benzene and 0.38 gram (7.24 millimoles) of acrylonitrile were heated at reflux temperature while progress of the reaction was monitored by TLC. After 2.5 hours, the reaction mixture was cooled to room temperature, and the mixture subjected to reduced pressure to vaporize the benzene solvent and excess acrylonitrile and to obtain a solid residue. The solid was recrystallized from acetonitrile/ethyl acetate to obtain a purified 4-(5H-dibenzo[a,d]cyclohepten-5-yl)-1-(2-cyanoethyl)piperidine product which after drying at 100° C. at 1 millimeter mercury pressure for 2 hours and at room temperature for 15 hours, melted at 165°-168° C. The yield of the product was 760 milligrams (64 percent). A second crop was obtained which after recrystallization from acetonitrile was in the form of white needles, m.p. 169°-170° C. The product had elemental analyses as follows:

Calcd for $C_{23}H_{24}N_2$: C, 84.11; H, 7.37; N, 8.53 Found: C, 83.83; H, 7.54; N, 8.53.

EXAMPLE V 4-(5H-Dibenzo[a,d]dicyclohepten-5-yl)-1-(2-carbamoylethyl)piperidine

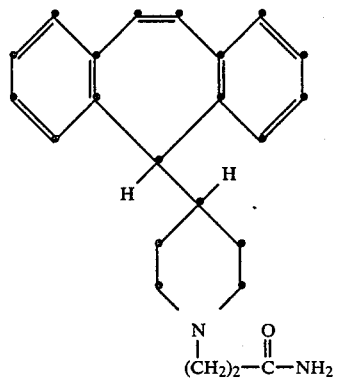

1.00 gram (3.62 millimoles) of 4-(5H-dibenzo-[a,d]cyclohepten-5-yl)piperidine, 0.26 gram (3.62 millimoles) of acrylamide, 0.04 gram (0.36 millimole) of triethylamine and 20 milliliters of isopropyl alcohol were stirred together at reflux temperature while protected from atmospheric moisture. A TLC analysis of a sample of the reaction mixture indicated presence of some piperidine compound but no acrylamide. 50 milligrams (0.7 millimole) of acrylamide in 1 milliliter of isopropyl alcohol was added and the reaction continued at reflux temperature for a total of about 3.5 hours. The reaction mixture was allowed to cool to room temperature and the solvent then removed in vacuo to obtain the desired 4-(5H-dibenzo[a,d]cyclohepten-5-yl)-1-(2-carbamoylethyl)piperidine product as residue. The crude product was crystallized from methylene chloride/hexane, then dried in vacuo overnight at 100° C. to obtain 900 milligrams (72 percent yield) of product, m.p. 135°–140° C.

EXAMPLE VI 4-(5H-Dibenzo[a,d]cyclohepten-5-yl)-1-(3-aminopropyl)piperidine

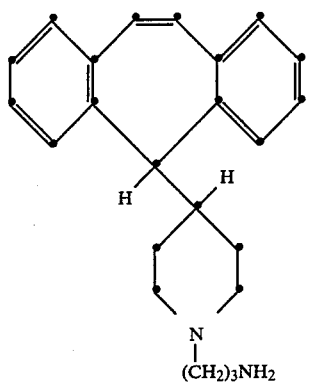

600 milligrams (1.73 millimoles) of 4-(5H-dibenzo[a,d]cyclohepten-5-yl)-1-(2-carbamoylethyl)piperidine in 8 milliliters of tetrahydrofuran was added to a stirred solution of 131 milligrams (3.46 millimoles) of lithium aluminum hydride in 10 milliliters of tetrahydrofuran under nitrogen atmosphere followed by a 2 milliliter wash. The mixture was stirred at room temperature for twenty hours. At this time TLC analysis of a sample of reaction mixture indicated 90 percent completion of reaction. The mixture was then heated to reflux and maintained at this temperature for 4 hours, then cooled in an ice bath and diluted to 50 milliliters with tetrahydrofuran. The reaction was then quenched by the n,n,3n method, dried (over magnesium sulfate), filtered and vaporized under reduced pressure to produce 370 milligrams of a yellow gum. Thin layer chromatographic analysis employing 5% methanol/95% chloroform/ammonia mixture as eluant showed the yellow gum to be primarily the desired 4-(5H-dibenzo[a,d]cyclohepten-5-yl)-1-(3-aminopropyl)piperidine product. The gum was purified by chromatographing on silica gel employing the same eluant mixture and thereby obtaining oily white crystals of the product which after recrystallization from acetonitrile melted at 146°–156° C. Elemental analyses of the product after drying were as follows:

Calcd for $C_{23}H_{28}N_2$: C, 83.09; H, 8.49; N, 8.43 Found: C, 82.92; H, 8.69; N, 8.54.

EXAMPLE VII 4-(5H-Dibenzo[a,d]cyclohepten-5-yl)-δ-oxo-1-piperidinepentanoic Acid

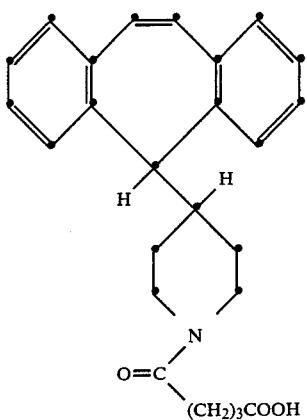

0.04 gram (0.36 millimole) of 4-dimethylaminopyridine, 0.94 gram (7.26 millimoles) of ethyl diisopropylamine, and 0.41 gram (3.63 millimoles) of glutaric anhydride were added successively to a solution of 1.00 gram (3.63 millimoles) of 4-(5H-dibenzo[a,d]cyclohepten-5-yl)-piperidine and the resulting mixture stirred at ambient temperature for two hours. The reaction mixture was diluted with 100 milliliters of methylene chloride and washed with aqueous hydrochloric acid and then with brine. The washed solution was dried over magnesium sulfate, the drying agent filtered and the solution evaporated in vacuo whereupon a foam was produced which when triturated with hot acetonitrile produced white crystals. The crystals were recrystalized from hot acetic acid/acetonitrile to obtain 4-(5H-dibenzo[a,d]cyclohepten-5-yl)-δ-oxo-1-piperidinepentanoic acid product, m.p. 180°–186° C. The product had elemental analyses as follows:

Calcd for $C_{25}H_{27}NO_3$: C, 77.09; H, 6.99; N, 3.60 Found: C, 77.15; H, 7.11; N, 3.67.

EXAMPLE VIII 4-(5H-Dibenzo[a,d]cyclohepten-5-yl)-1-(p-fluorobenzoyl)piperidine

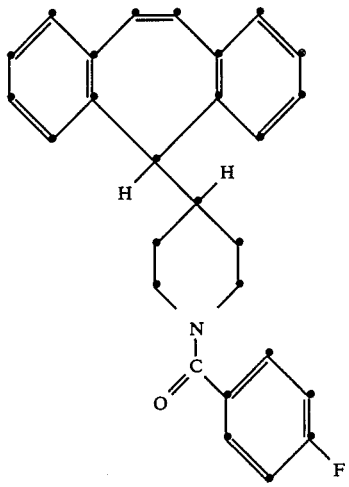

0.64 gram (4.03 millimoles) of p-fluorobenzoyl chloride, 1.84 grams (18.2 millimoles) of triethylamine, 0.22 gram (1.82 millimoles) of 4-dimethylaminopyridine was added at ambient temperature to a solution of 1.00 gram (3.63 millimoles) of 4-(5H-dibenzo[a,d]cyclohepten-5-yl)piperidine in 40 milliliters of dry methylene chloride while protected from atmospheric moisture and the mixture stirred for a total of about 50 minutes. About 10 grams of ice was added to the reaction mixture to quench the reaction and the resulting biphasic mixture stirred and allowed to warm to room temperature. The aqueous and organic phases were separated and the organic phase washed successively with 5 percent hydrochloric acid, aqueous bicarbonate and brine. The washed solution was dried over magnesium sulfate, the drying agent then filtered off and the solvent vaporized in vacuo to obtain 1.54 grams of 4-(5H-dibenzo[a,d]cyclohepten-5-yl)-1-(p-fluorobenzoyl)piperidine residue which crystallized in a few hours at ambient temperature. Recrystallization from toluene produced white needles. The product had a melting point of 150°–151° C. Elemental analyses indicated presence of solvent of crystallization; the results calculated for 1 mole of toluene of crystallization were as follows:

Calc'd for $C_{34}H_{32}FNO$: C, 83.40; H, 6.59; N, 2.86. Found: C, 83.39; H, 6.63; N, 3.11.

EXAMPLE IX 4-(5H-Dibenzo[a,d]cyclohepten-5-yl)-1-piperidine carboximidamide hydrochloride

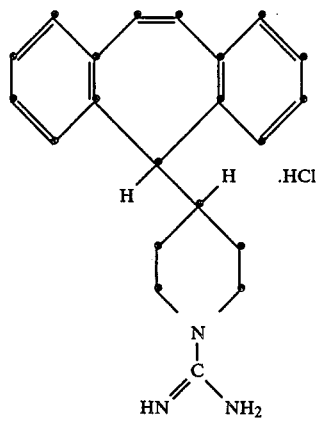

4-(5H-Dibenzo[a,d]cyclohepten-5-yl)piperidine hydrochloride starting material was first prepared by adding concentrated hydrochloric acid to a solution of 0.73 gram (2.34 millimoles) of 4-(5H-dibenzo[a,d]cyclohepten-5-yl)piperidine in hot ethanol until the solution was acidic, then vaporizing the solvent to obtain a residue, and recrystallizing the residue from methanol/ethyl acetate.

The amine hydrochloride so prepared was mixed together with 0.19 gram (4.68 millimoles) of cyanamide and 10 milliliters of methanol and the resulting mixture heated at reflux temperature for four days. Thin layer chromatographic analysis showed substantially no reaction had occurred. The methanol was replaced with 15 milliliters of n-butanol and the mixture heated at reflux temperature for a total of eight days. During this period it was observed that on the fifth day the mixture became homogenous and on the sixth day a white precipitate had formed. At the end of the eighth day, the mixture was cooled to room temperature, the precipitate filtered off, and dried at 100° C./1 mm Hg for 5 hours to a constant weight. The material did not melt or decompose below 340° C. Analysis showed the compound to be 4-(5H-dibenzo(a,d)cyclohepten-5-yl)-1-piperidinecarboximidamide hydrochloride. Elemental analyses were as follows:

Calc'd for $C_{21}H_{24}ClN_3$: C, 71.27; H, 6.84; N, 11.87. Found: C, 71.54 ; H, 7.05; N, 11.77.

EXAMPLE X 4-(5H-Dibenzo[a,d]cyclohepten-5-yl)-1-piperidinecarbothioaldehyde

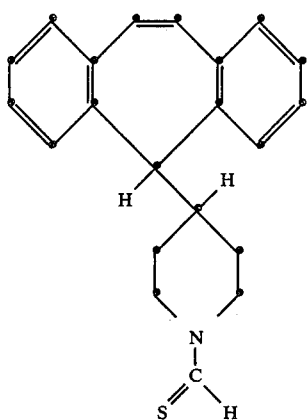

0.78 gram (8.77 millimoles) of dimethylthioformamide was added to a solution of 1.21 grams (4.39 millimoles) of 4-(5H-dibenzo[a,d]cyclohepten-5-yl)piperidine in 20 milliliters of toluene and the resulting mixture heated at reflux temperature for 18 hours and 45 minutes. Thin layer chromatographic analysis indicated the presence of a small amount of new substance. Another 0.5 milliliter of dimethylthioformamide was added and the mixture continued to be heated at reflux temperature for 28 hours. The reaction mixture was then cooled to room temperature and diluted to 100 milliliters with toluene, the diluted solution washed with four 50 milliliter portions of distilled water and dried over magnesium sulfate. The drying agent and solvent were removed in a manner similar to that previously described to obtain a yellow oil as residue which crystallized on standing overnight. The solid was recrystallized from acetonitrile to obtain cream colored crystals of 4-(5H-dibenzo[a,d]cyclohepten-5-yl)-1-piperidine carbothioaldehyde product in a yield of 900 milligrams (64 percent). The product after drying at 100° C. at 1 millimeter mercury pressure had a melting point of 186°–189° C. Elemental analyses were as follows:

Calc'd for $C_{21}H_{21}SN$: C, 78.95; H, 6.63; N, 4.38. Found: C, 78.92; H, 6.78; N, 4.44.

EXAMPLE XI 4-(5H-Dibenzo(a,d)cyclohepten-5-yl)-1-piperidine carboxaldehyde

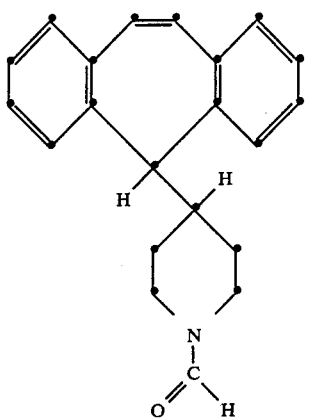

1.00 gram (3.62 millimoles) of 4-(5H-dibenzo[a,d]cyclohepten-5-yl)piperidine, 0.23 gram (3.62 millimoles) of powdered copper, 1.41 grams (10.9 millimoles) of ethyl diisopropylamine, 0.74 gram (3.62 moles) of iodobenzene, and 20 milliliters of dimethylformamide were mixed together in an atmosphere of nitrogen and heated with stirring at reflux temperature for 32 hours. Thereafter, the mixture was allowed to cool to room temperature, filtered through a pad of celite and the filtrate taken up in 150 milliliters of ethyl acetate. The ethyl acetate solution was washed four times with 50 milliliter portions of water and once with 100 milliliter portion of brine, dried over magnesium sulfate, and then subjected to reduced pressure to vaporize the solvent and to obtain a crystalline brown solid which was purified by chromatographing on silica with 75/25 ethyl acetate/hexane. The thus purified material was recystallized twice from acetonitrile to obtain a product having a melting point of 193°-195°. The product was found to be 4-(5H-dibenzo(a,d)cyclohepten-5-yl)-1-piperidine carboxaldehyde. Elemental analyses were as follows:

Calc'd for $C_{21}H_{21}NO$: C, 83.13; H, 6.98; N, 4.62. Found: C, 83.24; H, 7.26; N, 4.72.

EXAMPLE XII 4-(5H-Dibenzo[a,d]cyclohepten-5-yl)-1-(methylsulfonyl)piperidine

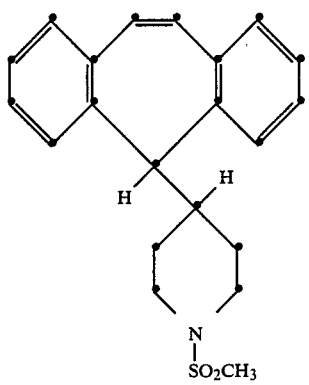

0.59 gram (5.17 millimoles) of mesyl chloride was added neat and in a dropwise manner over a 5 minute period to a stirred solution of 1.00 gram (3.62 millimoles) of 4-(5H-dibenzo[a,d]cyclohepten-5-yl)-piperidine and 1.45 grams (14.35 millimoles) of triethylamine in 10 milliliters of methylene chloride. The resulting solution was stirred an additional one-half hour and then diluted with 100 milliliters of methylene chloride. Thereafter the solution was washed with saturated sodium bicarbonate solution, then with brine and dried over magnesium sulfate. The drying agent was filtered off and the solvent vaporized in vacuo to obtain the desired 4-(5H-dibenzo[a,d]cyclohepten-5-yl)-1-(methylsulfonyl)piperidine product as a yellow solid residue. The product after recrystallization from ethyl acetate had a melting point of 260°-268° C. and elemental analyses as follows:

Calc'd for $C_{21}H_{23}NO_2S$: C, 71.36; H, 6.56; N, 3.96. Found: C, 70.96; H, 6.82; N, 3.91.

EXAMPLE XIII 8-(4-(5H-Dibenzo[a,d]cyclohepten-5-yl)-1-piperidinyl)imidazo[1,2a]pyrazine

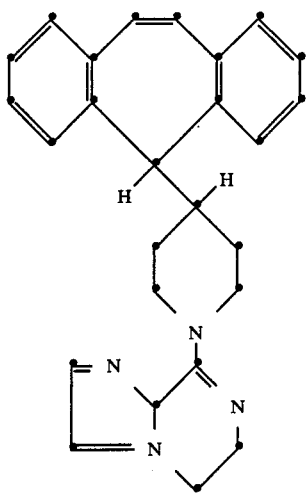

1.00 gram (3.62 millimoles) of 4-(5H-dibenzo[a,d]cyclohepten-5-yl)-1-piperidine, 0.56 gram (3.62 millimoles) 8-chloroimidazo[1,2a]pyrazine, 0.94 gram (7.25 millimoles) of diisopropyl ethylamine and 20 milliliters of n-butanol were stirred together and heated at reflux temperature for 16½ hours whereupon a reaction took place with the consumption of 8-chloroimidazo[1,2a]pyrazine (as indicated by thin layer chromatographic analysis) and the formation of 8-(4-(5H-dibenzo[a,d]cyclohepten-5-yl)-1-piperidinyl)imidazo[1,2a]pyrazine product in the reaction mixture. The reaction mixture was allowed to cool to room temperature and the solvent vaporized in vacuo to obtain a residue. The residue was partitioned between ethyl acetate and 10 percent sodium hydroxide solution. The ethyl acetate solution containing the product was washed with brine and dried over magnesium sulfate. The dried solution then was filtered through a pad of silica gel and the filtrate subjected to reduced pressure to vaporize the solvent and recover a semi-solid mass which was crystallized from 1:1 acetonitrile/ethyl acetate to obtain 891 milligrams (62 percent yield) of the product as brown crystals which after drying at 100° C. at 1 millimeter of mercury pressure for 3 hours had a melting point of 188°-191° C. Elemental analyses of the product were as follows:

Calc'd for $C_{26}H_{24}N_4$: C, 79.56; H, 6.16; N, 14.27. Found: C, 79.27; H, 6.38; N, 14.28.

EXAMPLE XIV 4-(5H-Dibenzo[a,d]cyclohepten-5-yl)-1-(3-fluoro-1-pyridyl)piperidine

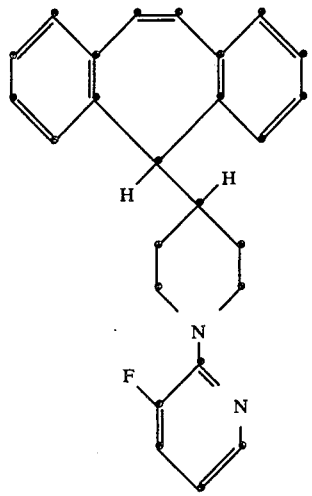

0.50 gram (1.82 millimoles) of 4-(5H-dibenzo[a,d]cyclohepten-5-yl)piperidine, 0.24 gram (1.82 millimoles) of 3-fluoro-2-chloropyridine, 0.47 gram (3.64 mole) of ethyl diisopropylamine and 10 milliliters of n-butanol were heated at reflux temperature protected from atmospheric moisture with a drying tube. After 19.25 hours heating, an additional 240 milligrams of the 3-fluoro-2-chloropyridine was added. After another 24 hours, 300 milligrams of ethyl dipropylamine was added and heating continued. After about 140 hours of refluxing, the mixture was concentrated, diluted with ether, washed successively with 10 percent aqueous sodium hydroxide and brine, dried, and the solvent vaporized to obtain a brown semi-solid residue. The residue was purified by chromatographing on silica gel with 7 percent ether in hexanes to obtain the 4-(5H-dibenzo[a,d]cyclohepten-5-yl)-1-(3-fluoro-1-pyridyl)piperidine product as a crystalline white solid, which after drying overnight in vacuo and 4 hours at 100° C. at 1 millimeter of mercury pressure had a melting point of 208°-210° C. Elemental analyses were as follows:

Calc'd for $C_{25}H_{23}FN_2$: C, 81.05; H, 6.26; N, 7.86. Found: C, 81.08; H, 6.42; N, 7.23.

EXAMPLE XV 4-(3-Chloro-5H-dibenzo[a,d]cyclohepten-5-yl)-1-(4-methoxybenzyl)piperidine

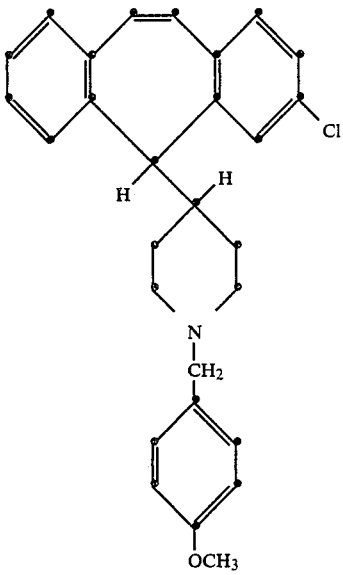

In an operation carried out in a manner similar to that described in Example I, 4-(3-chloro-5H-dibenzo[a,d]cyclohepten-5-yl)-1-(4-methoxybenzyl)piperidine is obtained by the reaction of 0.957 gram (3.47 millimoles) of 4-5-H-dibenzo[a,d]cyclohepten-5-yl)piperidine, 0.472 gram (3.47 millimoles) of p-methoxybenzaldehyde, 0.63 gram (10 millimoles) of sodium cyanoborohydride and 10 milliliters of ethanol.

EXAMPLE XVI

In similar operations, the following compounds may be prepared:
4-(5H-Dibenzo[a,d]cyclohepten-5-yl)-1-(4-isopropoxybenzyl)piperidine by the reaction of 4-(5H-dibenzo[a,d]cyclohepten-5-yl)piperidine, 4-isopropoxybenzaldehyde and sodium cyanoborohydride in ethanol.
4-(10,11-Dihydro-5H-dibenzo[a,d]-cyclohepten-5-yl)-1-(4-diethylaminobenzyl)piperidine by the reaction of 4-(10,11-dihydro-5H-dibenzo[a,d]-cyclohepten-5-yl)piperidine, 4-diethylaminobenzaldehyde and sodium cyanoborohydride in ethanol.
4-(3-Methyl-5H-dibenzo[a,d]cyclohepten-5-yl)-1-(4-(ethylmethylamino)benzyl)piperidine by the reaction of 4-(3-methyl-5H-dibenzo[a,d]cyclohepten-5-yl)piperidine, 4-(ethylmethylamino)benzaldehyde and sodium cyanoborohydride in ethanol.
4-(3-Bromo-10,11-dihydro-5H-dibenzo[a,d]cyclohepten-5-yl)-1-(4-di(n-propyl)aminobenzyl)piperidine by the reaction of 4-(3-bromo-10,11-dihydro-5H-dibenzo[a,d]cyclohepten-5-yl)piperidine, 4-di(n-propyl)aminobenzaldehyde and sodium cyanoborohydride in ethanol.
4-(2-Chloro-10,11-dihydro-5H-dibenzo[a,d]cyclohepten-5-yl)-1-(4-(n-pentoxy)benzyl)piperidine by the reaction of 4-(2-chloro-10,11-dihydro-5H-dibenzo[a,d]cyclohepten-5-yl)piperidine, 4-(n-pentoxy)benzaldehyde and sodium cyanoborohydride in ethanol.
4-(3-Trifluoromethyl-5H-dibenzo[a,d]cyclohepten 5-yl)-1-(2-(4-dimethylaminophenyl)ethyl)piperidine by the reaction of 4-(3-trifluoromethyl-5H-dibenzo[a,d-]cyclohepten-5-yl)piperidine, 2-(4-dimethylaminophenyl)acetaldehyde and sodium cyanoborohydride in ethanol.

4-(2-Methoxy-5H-dibenzo[a,d]cyclohepten-5-yl)-1-(2-(4-methoxyphenyl)ethyl)piperidine by the reaction of 4-(2-methoxy-5H-dibenzo[a,d]cyclohepten-5-yl)piperidine and 2-(4-methoxyphenyl)acetaldehyde.

4-(3-Bromo-10,11-dihydro-5H-dibenzo[a,d]cyclohepten-5-yl)-1-(3-(4-dimethylaminophenyl)propyl)piperidine by the reaction of 4-(3-bromo-10,11-dihydro-5H-dibenzo[a,d]cyclohepten-5-yl)piperidine and 3-(4-dimethylaminophenyl)propionaldehyde.

EXAMPLE XVII

In operations carried out in a manner similar to that described in Example II, the following compounds may be prepared:

4-(3-Bromo-5H-dibenzo[a,d]cyclohepten-5-yl)-1-(3-(3,5-diethyoxyphenyl)prop-2-en-1-yl)piperidine from 4-(3-bromo-5H-dibenzo[a,d]-cyclohepten-5-yl)piperidine and 3,5-dimethoxycinnamoyl chloride to obtain 4-(3-bromo-5H-dibenzo[a,d]cyclohepten-5-yl)-1-(3,5-diethoxycinnamoyl)piperidine followed by the reduction of the latter with lithium aluminum hydride.

4-(3-Chloro-10,11-dihydro-5H-dibenzo[a,d]cyclohepten-5-yl)-1-cinnamylpiperidine from 4-(3-chloro-9,10-dihydro-5H-dibenzo[a,d]cyclohepten-5-yl)piperidine and cinnamoyl chloride to obtain 4-(3-chloro-10,11-dihydro-5H-dibenzo[a,d]cyclohepten-5-yl)-1-cinnamoylpiperidine followed by the reduction of the latter with lithium aluminum hydride.

4-(3-Methoxy-10,11-dihydro-5H-dibenzo[a,d]cyclohepten-5-yl)-1-cinnamylpiperidine from 4-(3-methoxy-10,11-dihydro-5H-dibenzo[a,d]cyclohepten-5-yl)piperidine and cinnamoyl chloride to obtain 4-(3-methoxy-10,11-dihydro-5H-dibenzo[a,d]cyclohepten-5-yl)-1-cinnamoylpiperidine followed by the reduction of the latter with lithium aluminum hydride.

4-(2-Trifluoromethyl-10,11-dihydro-5H-dibenzo[a,d-]cyclohepten-5-yl)-1-cinnamylpiperidine from 4-(2-trifluoromethyl-10,11-dihydro-5H-dibenzo[a,d]cyclohepten-5-yl)piperidine and cinnamoyl chloride to obtain 4-(2-trifluoromethyl,10,11-dihydro-5H-dibenzo[a,d]cyclohepten-5-yl)-1-cinnamoylpiperidine followed by the reduction of the latter with lithium aluminum hydride.

EXAMPLE XVIII

In operations carried out in a manner similar to that described in Example IV, the following compounds my be prepared:

4-(4-Fluoro-5H-dibenzo[a,d]cyclohepten-5-yl)-1-(2-cyanoethyl)piperidine by the reaction of 4-(4-fluoro-5H-dibenzo[a,d]cyclohepten-5-yl)piperidine and acrylonitrile.

4-(3-Ethoxy-5H-dibenzo[a,d]cyclohepten-5-yl)-1-(2-cyanoethyl)piperidine by the reaction of 4-(3-ethoxy-5H-dibenzo[a,d]cylohepten-5-yl)piperidine and acrylonitrile.

4-(2-Iodo-10,11-dihydro-5H-dibenzo[a,d]-cyclohepten-5-yl)-1-(2-cyanoethyl)piperidine by the reaction of 4-(2-iodo-10,11-dihydro-5H-dibenzo[a,d]cyclohepten-5-yl)piperidine and acrylonitrile.

4-(1-Methoxy-10,11-dihydro-5H-dibenzo[a,d]cyclohepten-5-yl)-1-(2-cyanoethyl)piperidine by the reaction of 4-(1-methoxy-10,11-dihydro-5H-dibenzo[a,d]cyclohepten-5-yl)piperidine and acrylonitrile.

EXAMPLE XIX

In operations carried out in a manner similar to that described in Example V, the following compounds may be prepared:

4-(3-Bromo-5H-dibenzo[a,d]cyclohepten-5-yl)-1-(2-carbamoylethyl)piperidine by the reaction of 4-(3-bromo-5H-dibenzo[a,d]cyclohepten-5-yl)piperidine and acrylamide.

4-(3-n-Butoxy-5H-dibenzo[a,d]cyclohepten-5-yl)-1-(2-carbamoylethyl)piperidine by the reaction of 4-(3-n-butoxy-5H-dibenzo[a,d]cyclohepten-5-yl)piperidine and acrylamide.

4-(10,11-Dihydro-5H-dibenzo[a,d]cyclohepten-5-yl)-1-(2-carbamoylethyl)piperidine by the reaction of 4-(10,11-dihydro-5H-dibenzo[a,d]cyclohepten-5-yl)piperidine and acrylamide.

4-(3-Fluoro-10,11-dihydro-5H-dibenzo[a,d]cyclohepten-5-yl)-1-(2-carbamoylethyl)piperidine by the reaction of 4-(3-fluoro-10,11-dihydro-5H-dibenzo[a,d]cyclohepten-5-yl)piperidine and acrylamide.

EXAMPLE XX

In operations carried out in a manner similar to that described in Example VI, the following compounds may be prepared by the reduction of the compounds of Example XIX with lithium aluminum hydride:

4-(3-Bromo-5H-dibenzo[a,d]cyclohepten-5-yl)-1-(3-aminopropyl)piperidine, 4-(3-n-Butoxy-5H-dibenzo[a,d]cyclohepten-5-yl)-1-(3-aminopropyl)piperidine.

4-(10,11-Dihydro-5H-dibenzo[a,d]cyclohepten-5-yl)-1-(3-aminopropyl)piperidine.

4-(3-Fluoro-10,11-dihydro-5H-dibenzo[a,d]cyclohepten-5-yl)-1-(3-aminopropyl)piperidine.

EXAMPLE XXI

In operations carried out in a manner similar to that described in Example VII, the following compounds may be prepared:

4-(3-Fluoro-5H-dibenzo[a,d]cylcohepten-5-yl)-δ-oxo-1-piperidinepentanoic acid from 4-(3-fluoro-5H-dibenzo[a,d]cyclohepten-5-yl)piperidine and glutaric anhydride.

4-(3-Trifluoromethyl-5H-dibenzo[a,d]cyclohepten-5-yl)-δ-oxo-1-piperidinepentanoic acid from 4-(3-trifluoromethyl-5H-dibenzo[a,d]cyclohepten-5-yl)piperidine and glutaric anhydride.

4-(3-Chloro-10,11-dihydro-5H-dibenzo[a,d]cyclohepten-5-yl)-δ-oxo-1-piperidinebutanoic acid from 4-(3-chloro-10,11-dihydro-5H-dibenzo[a,d]cyclohepten-5-yl)piperidine and succinic anhydride.

4-(2-Ethoxy-10,11-dihydro-5H-dibenzo[a,d]cyclohepten-5-yl)-γ-oxo-1-piperidinebutanoic acid from 4-(2-ethoxy-10,11-dihydro-5H-dibenzo[a,d]cylcohepten-5-yl)piperidine and succinic anhydride.

4-(3-Iodo-10,11-dihydro-5H-dibenzo[a,d]cyclohepten-5-yl)-β-oxo-1-piperidinepropionic acid from 4-(3-iodo-10,11-dihydro-5H-dibenzo[a,d]cyclohepten-5-yl)piperidine and malonic anhydride.

EXAMPLE XXII

In operations carried out in a manner similar to that described in Example VIII, the following compounds may be prepared:

4-(4-Fluoro-5H-Dibenzo[a,d]cyclohepten-5-yl)-1-benzoylpiperidine by the reaction of 4-(4-fluoro-5H-dibenzo[a,d]cyclohepten-5-yl)piperidine and benzoyl chloride.

4-(2-Chloro-5H-dibenzo[a,d]cyclohepten-5-yl)-1-acetylpiperidine by the reaction of 4-(2-chloro-5H-dibenzo[a,d]cyclohepten-5-yl)piperidine and acetyl chloride.

4-(3-Iodo-10,11-dihydro-5H-dibenzo[a,d]cyclohepten-5-yl)-1-trichloroacetylpiperidine by the reaction of 4-(3-iodo-10,11-dihydro-5H-dibenzo[a,d]cyclohepten-5-yl)piperidine and trichloroacetyl chloride.

4-(3-Methoxy-5H-dibenzo[a,d]cyclohepten-5-yl)-1-trichloroacetylpiperidine by the reaction of 4-(3-iodo-10,11-dihydro-5H-dibenzo[a,d]cyclohepten-5-yl)piperidine and trichloroacetyl chloride.

4-(3-Methoxy-5H-dibenzo[a,d]cyclohepten-5-yl)-1-(2-chlorobenzoyl)piperidine by the reaction of 4-(3-methoxy-5H-dibenzo[a,d]cyclohepten-5-yl) piperidine and 2-chlorobenzoyl chloride.

4-(2-Ethoxy-10,11-dihydro-5H-dibenzo[a,d]cyclohepten-5-yl)-1-(4-bromobenzoyl)-piperidine by the reaction of 4-(2-ethoxy-10,11-dihydro-5H-dibenzo[a,d]cyclohepten-5-yl)piperidine and 4-bromobenzoyl chloride.

4-(2,4-Dichloro-10,11-dihydro-5H-dibenzo[a,d]cyclohepten-5-yl)-1-(2,4-dichlorobenzoyl)piperidine by the reaction of 4-(2,4-dichloro-10,11-dihydro-5H-dibenzo[a,d]cyclohepten-5-yl)piperidine and 2,4-dichlorobenzoyl chloride.

4-(3-Bromo-10,11-dihydro-5H-dibenzo[a,d]cyclohepten-5-yl)-1-(p-toluoyl)piperidine by the reaction of 4-(3-bromo-10,11-dihydro-5H-dibenzo[a,d]cyclohepten-5-yl)piperidine and p-toluoyl chloride.

4-(2-Chloro-5H-dibenzo[a,d]cyclohepten-5-yl)-1-(2,4-dimethylbenzoyl)piperidine by the reaction of 4-(2-chloro-5H-dibenzo[a,d]cyclohepten-5-yl)piperidine and 2,4-dimethylbenzoyl chloride.

EXAMPLE XXIII

In operations carried out in a manner similar to that described in Example IX, the following compounds may be prepared.

4-(3-Chloro-5H-dibenzo[a,d]cyclohepten-5-yl)-1-piperidine carboximidamide hydrochloride by the reaction of 4-(3-chloro-5H-dibenzo[a,d]cyclohepten-5-yl)-1-piperidine hydrochloride and cyanamide.

4-(3-Methoxy-5H-dibenzo[a,d]cyclohepten-5-yl)-1-piperidine carboximidamide hydrochloride by the reaction of 4-(3-methoxy-5H-dibenzo[a,d]cyclohepten-5-yl)-1-piperidine hydrochloride and cyanamide.

4-(3-Bromo-10,11-dihydro-5H-dibenzo[a,d]cyclohepten-5-yl)-1-piperidine carboximidamide hydrochloride by the reaction of 4-(3-bromo-10,11-dihydro-5H-dibenzo[a,d]cyclohepten-5-yl)piperidine hydrochloride and cyanamide.

4-(1-Fluoro-10,11-dihydro-5H-dibenzo[a,d]cylohepten-5-yl)-1-piperidine carboxamide hydrochloride by the reaction of 4-(1-fluoro-10,11-dihydro-5H-dibenzo[a,d]cyclohepten-5-yl)piperidine hydrochloride and cyanamide.

4-(10,11-Dihydro-5H-dibenzo[a,d]cyclohepten-5-yl)-1-piperidine carboxamide hydrochloride by the reaction of 4-(10,11-dihydro-5H-dibenzo[a,d]cyclohepten-5-yl)piperidine hydrochloride and cyanamide.

EXAMPLE XXIV

In operations carried out in a manner similar to that described in Example X, the following compounds may be prepared:

4-(2-Chloro-5H-dibenzo[a,d]cyclohepten-5-yl)-1-piperidinecarbothioaldehyde by the reaction of 4-(2-chloro-5H-dibenzo[a,d]cyclohepten-5-yl)piperidine and dimethylthioformamide.

4-(1-Methoxy-10,11-dihydro-5H-dibenzo[a,d]cyclohepten-5-yl)-1-piperidinecarbothioaldehyde by the reaction of 4-(1-methoxy-10,11-dihydro-5H-dibenzo[a,d]cyclohepten-5-yl)piperidine and dimethylthioformamide.

4-(3-Bromo-10,11-dihydro-5H-dibenzo[a,d]cyclohepten-5-yl)-1-piperidinecarbothioaldehyde by the reaction of 4-(3-bromo-10,11-dihydro-5H-dibenzo[a,d]cyclohepten-5-yl)piperidine and dimethylthioformamide.

4-(3-Iodo-5H-dibenzo[a,d]cyclohepten-5-yl)-1-piperidinecarboxaldehyde by the reaction of 4-(3-iodo-5H-dibenzo[a,d]cyclohepten-5-yl)piperidine and dimethylformamide.

4-(2-Ethoxy-10,11-dihydro-5H-dibenzo[a,d]cyclohepten-5-yl)-1-piperidinecarboxaldehyde by the reaction of 4-(2-ethoxy-10,11-dihydro-5H-dibenzo[a,d]cyclohepten-5-yl)piperidine and dimethylformamide.

EXAMPLE XXV

In operations carried out in a manner similar to that described in Example XII, the following compounds may be prepared:

4-(3-Fluoro-5H-dibenzo[a,d]cyclohepten-5-yl)-1-(ethylsulfonyl)piperidine by the reaction of 4-(3-fluoro-5H-dibenzo[a,d]cyclohepten-5-yl)piperidine and ethylsulfonyl chloride.

4-(3-Methoxy-5H-dibenzo[a,d]cyclohepten-5-yl)-1-(isobutylsulfonyl)piperidine by the reaction of 4-(3-methoxy-5H-dibenzo[a,d]cyclohepten-5-yl)piperidine and isobutylsulfonyl chloride.

4-(3-Bromo-10,11-dihydro-5H-dibenzo[a,d]cyclohepten-5-yl)-1-(isopropylsulfonyl)piperidine by the reaction of 4-(3-bromo-10,11-dihydro-5H-dibenzo[a,d]cyclohepten-5-yl)piperidine and isopropylsulfonyl chloride.

4-(3-Isopropyl-10,11-dihydro-5H-dibenzo[a,d]cyclohepten-5-yl)-1-(methylsulfonyl)piperidine by the reaction of 4-(3-isopropyl-10,11-dihydro-5H-dibenzo[a,d]cyclohepten-5-yl)piperidine and mesyl chloride.

EXAMPLE XXVI

In operations carried out in a manner similar to that described in Example XIII and XIV, the following compounds may be prepared:

4-(3-Methoxy-5H-dibenzo[a,d]cyclohepten-5-yl)-1-(3-fluoro-1-pyridyl)piperidine by the reaction of 4-(3-methoxy-5H-dibenzo[a,d]cyclohepten-5-yl)piperidine and 3-fluoro-2-chloropyridine.

4-(3-Chloro-10,11-dihydro-5H-dibenzo[a,d]cyclohepten-5-yl)-1-(3-chloro-1-pyridyl)piperidine by the reaction 4-(3-chloro-10,11-dihydro-5H-dibenzo[a,d]cyclohepten-5-yl)piperidine and 2,3-dichloropyridine.

8-(4-(3-Bromo-5H-dibenzo[a,d]cyclohepten-5-yl)-1-piperidinyl)imidazo[1,2a]pyrazine by the reaction of 4-(3-bromo-5H-dibenzo[a,d]cyclohepten-5-yl)-1-piperidine and 8-chloroimidazo[1,2a]pyrazine.

8-(4-(2-Ethoxy-10,11-dihydro-5H-dibenzo[a,d]cyclohepten-5-yl)-1-piperidinyl)imidazo[1,2a]pyrazine by the reaction of 4-(2-ethoxy-10,11-dihydro-5H-dibenzo[a,d]cyclohepten-5-yl)piperidine and 8-chloroimidazo[1,2a]pyrazine.

EXAMPLE XXVII

Tablets are prepared from a tablet composition comprising:

| | |
|---|---|
| 4-(5H—dibenzo[a,d]cyclohepten-5-yl)-1-(4-dimethylaminobenzyl)piperidine | 0.2 part by weight |
| Magnesium stearate | 1 part by weight |
| Polyvinylpyrrolidine | 4 part by weight |
| Talc | 5 part by weight |
| Starch | 10 part by weight |
| Lactose | 137.8 part by weight |
| Dimethylsilicone oil | 0.5 part by weight |
| Polyethylene glycol 6000 | 1.5 part by weight | by intimately blending the dry ingredients, thereafter adding the liquid ingredients and feeding into a tablet press to obtain the desired tablets containing 0.2 milligram of the active ingredient.

EXAMPLE XXVIII

Capsules for oral use each containing 1 milligram of 4-(5H-dibenzo[a,d]cyclohepten-5-yl)-1-cinnamylpiperidine are prepared by blending 1 gram of said piperidine compound with 287 grams of lactose and 4.1 grams of magnesium stearate. This is then used to fill 1000 capsules each containing 1 milligram of the piperidine compound.

EXAMPLE XXIX

An injectable solution employing 4-(5H-dibenzo[a,d]cyclohepten-5-yl)-1-(3,4,5-trimethoxycinnamyl)piperidine is prepared by mixing 1 gram of said piperidine compound, 9 grams of sodium chloride and distilled water to 1 liter. One milliliter portions of said solution may be employed to administer 1 milligram of 4-(5H-dibenzo[a,d]cyclohepten-5-yl)-1-(3,4,5-trimethoxycinnamyl)piperidine.

EXAMPLE XXX

A liquid suspension may be prepared by mixing together 5.0 grams of 4-(5H-dibenzo[a,d]cyclohepten-5-yl)-1-(3-aminopropyl)piperidine, 3.0 grams of Vee gum clay, 1.0 gram of methyl paraben, 10.0 grams of kaolin, 250 grams of glycerine and water to 1 liter. The suspension may be administered in an amount suitable for supplying the desired dose of 4-(5H-dibenzo[a,d]cyclohepten-5-yl)-1-(3-aminopropyl)piperidine.

EXAMPLE XXXI

The following salts may be prepared by intimately mixing the piperidine compound prepared as previously described with an ethanolic solution of the acid and thereafter recovering the salt.

4-(5H-Dibenzo[a,d]cyclohepten-5-yl)-1-(4-dimethylaminobenzyl)piperidine hydrogen phosphate.

4-(5H-Dibenzo[a,d]cyclohepten-5-yl)-1-cinnamylpiperidine hydrogen maleate.

4-(5H-Dibenzo[a,d]cyclohepten-5-yl)-1-(3,4,5-trimethoxycinnamyl)piperidine hydrochloride.

4-(5H-Dibenzo[a,d]cyclohepten-5-yl)-1-(3-aminopropyl)piperidine hydrogen tartrate.

What is claimed is:
1. A compound of the formula:

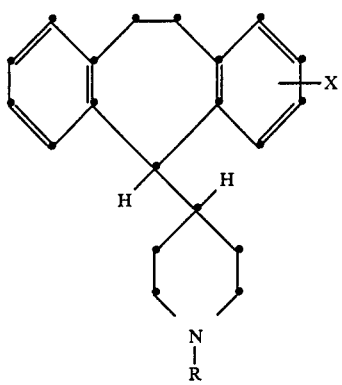

wherein:
the ⁝⁝⁝⁝ bond designation between the 10 and 11 positions indicates that the bond may be a saturated single bond or an unsaturated double bond,
X is hydrogen, halogen, trifluoromethyl or lower alkoxy;
R is selected from the group consisting of:
(a) a substituted aralkyl group represented by the formula:

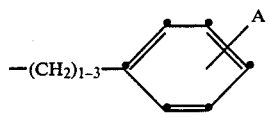

wherein A is di(lower alkyl)amino when the 10-11 bond is unsaturated;
(b) a nitrogen containing alkyl group represented by the formula:

—CH$_2$CH$_2$Y wherein Y is —CN, or

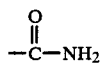

(c) an acyl group represented by the formula:

wherein R' is lower alkyl, substituted lower alkyl, phenyl or substituted phenyl, styryl or substituted styryl wherein substituted lower alkyl means a lower alkyl group which is substituted with halogen or ω-carboxy, substituted phenyl means a phenyl group which is substituted with halogen or lower alkyl, and substituted styryl means a group which is substituted with lower alkoxy;
(d) an imido group represented by the formula

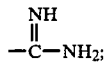

(e) a formyl group represented by the formula:

wherein Z is oxygen or sulfur;

(f) an alkyl sulfonyl group represented by the formula:

—SO$_2$—R"

wherein R" is lower alkyl;

(g) a heteroaryl group represented by the formula

wherein the dotted line represents a residue of a heterocyclic ring, wherein said heteroaryl group is selected from imidazopyrazinyl and halopyridyl;

or an acid addition salt.

2. A compound according to claim 1 wherein the bond between the 10 and 11 positions is an unsaturated double bond.

3. A compound according to claim 2 wherein X is (a) hydrogen or (b) halogen, trifluoromethyl or lower alkoxy in the 3-position wherein lower is meant from 1 to 6 carbon atoms.

4. A compound according to claim 3 wherein X is hydrogen and R is a substituted aralkyl group represented by the formula

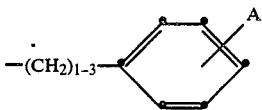

wherein A is di(lower alkyl)amino.

5. A compound according to claim 4 wherein R is 4-dimethylaminobenzyl, and which is named 4-(5H-dibenzo[a,d]cyclohepten-5-yl)-1-(4-dimethylaminobenzyl)piperidine.

6. A compound according to claim 3 wherein X is hydrogen and R is a nitrogen containing alkyl group represented by the formula

—CH$_2$CH$_2$Y wherein Y is —CN, or

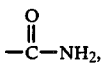

7. A compound according to claim 6 wherein X is hydrogen and R is —CH$_2$CH$_2$CN and which is named 4-(5H-dibenzo[a,d]cyclohepten-5-yl)-1-(2-cyanoethyl)piperidine.

8. A compound according to claim 3 wherein X is hydrogen and R is an acyl group represented by the formula

wherein R' is lower alkyl, substituted lower alkyl, phenyl or substituted phenyl, styryl or substituted styryl, wherein substituted means a substituent selected from halogen and lower alkyl.

9. A compound according to claim 8 wherein the acyl group is p-fluorobenzoyl and which is named 4-(5H-dibenzo[a,d]cyclohepten-5-yl)-1-(p-fluorobenzoyl)-piperidine.

10. A compound according to claim 3 wherein X is hydrogen and R is an amido group represented by the formula

and which is named 4-(5H-dibenzo[a,d]cyclohepten-5-yl)-1-piperidinecarboximidamide.

11. A compound according to claim 3 wherein X is hydrogen and R is a formyl group represented by the formula

wherein Z is oxygen or sulfur.

12. A compound according to claim 3 wherein X is hydrogen and R is an alkyl sulfonyl group represented by the formula —SO$_2$R" wherein R" is a lower alkyl.

13. A compound according to claim 3 wherein X is hydrogen and R is a heteroaryl group represented by the formula

wherein the dotted line represents a residue of a heterocyclic ring and wherein said heteroaryl group is selected from imidazopyrazinyl and halopyridyl.

14. A pharmaceutical composition useful for treating cardiovascular disorder caused by high cellular concentration of Ca$^{++}$ comprising a therapeutically effective amount of a compound of represented by the formula:

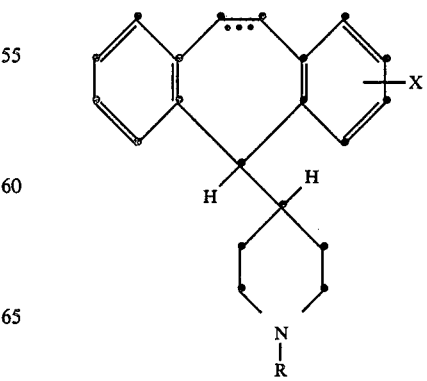

wherein:
 the ⁓ bond designation between the 10 and 11 positions indicates that the bond may be a saturated single bond or an unsaturated double bond, 'X is hydrogen, halogen, trifluoromethyl or lower alkoxy;
R is selected from the group consisting of:
 (a) a substituted aralkyl group represented by the formula:

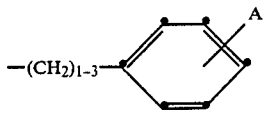

wherein A is di(lower alkyl)amino when the 10-11 bond is unsaturated;
 (b) a nitrogen containing alkyl group represented by the formula:

—CH₂CH₂Y wherein Y is —CN, or

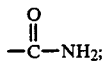

(c) an acyl group represented by the formula:

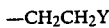

wherein R' is lower alkyl, substituted lower alkyl, phenyl or substituted phenyl, styryl or substituted styryl wherein substituted lower alkyl means a lower alkyl group which is substituted with halogen or ω-carboxy, substituted phenyl means a phenyl group which is substituted with halogen or lower alkyl, and substituted styryl means a group which is substituted with lower alkoxy;
 (d) an imido group represented by the formula

(e) a formyl group represented by the formula:

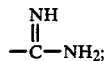

wherein Z is oxygen or sulfur;
 (f) an alkyl sulfonyl group represented by the formula:

—SO₂—R"

wherein R" is lower alkyl;
 (g) a heteroaryl group represented by the formula

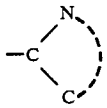

wherein the dotted line represents a residue of a heterocyclic ring, wherein said heteroaryl group is selected from imidazopyrazinyl and halopyridyl;
or an acid addition salt in admixture with a pharmaceutically acceptable carrier.

15. A method of treating cardiovascular disorders caused by high cellular concentration of Ca⁺⁺ comprising administering to a patient in need of such treatment, a therapeutically effective amount of a compound of the formula:

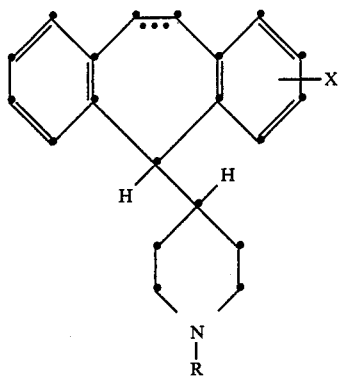

wherein:
 the ⁓ bond designation between the 10 and 11 positions indicates that the bond may be a saturated single bond or an unsaturated double bond,
X is hydrogen, halogen, trifluoromethyl or lower alkoxy;
R is selected from the group consisting of:
 (a) a substituted aralkyl group represented by the formula:

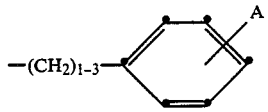

wherein A is di(lower alkyl)amino or lower alkoxy;
 (b) an aralkenyl group represented by the formula:

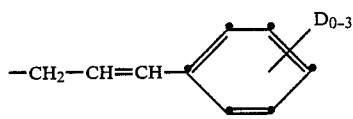

where D is lower alkoxy;
 (c) a nitrogen containing alkyl group represented by the formula:

—CH₂CH₂Y wherein Y is —CN, or

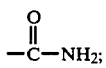

(d) an acyl group represented by the formula:

wherein R' is lower alkyl, substituted lower alkyl, phenyl or substituted phenyl, styryl or substituted styryl wherein substituted lower alkyl means a lower alkyl group which is substituted with halogen or ω-carboxy, substituted phenyl means a phenyl group which is substituted with halogen or lower alkyl, and substituted styryl means a group which is substituted with lower alkoxy;

(e) an imido group represented by the formula

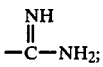

(f) a formyl group represented by the formula:

wherein Z is oxygen or sulfur;

(g) an alkyl sulfonyl group represented by the formula:

wherein R" is lower alkyl;

(h) a heteroaryl group represented by the formula

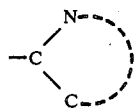

wherein the dotted line represents a residue of a heterocyclic ring, wherein said heteroaryl group is selected from imidazopyrazinyl and halopyridyl;

or an acid addition salt.

16. A method according to claim 15 wherein in said compound X is hydrogen and R is an aralkenyl group represented by the formula

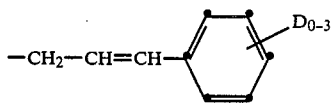

where D is lower alkoxy.

17. A method according to claim 16 wherein R is cinnamyl, and which is named 4-(5H-dibenzo[a,d]cyclohepten-5-yl)-1-cinnamylpiperidine.

18. A method according to claim 16 wherein R is 3-(3,4,5-trimethoxyphenyl)prop-2-en-1-yl, and which is named 4-(5H-dibenzo[a,d]cyclohepten-5-yl)-1-(3-(3,4,5-trimethoxyphenyl)prop-2-en-1-yl)piperidine.

* * * * *